(12) United States Patent
Kurokawa et al.

(10) Patent No.: US 7,576,051 B2
(45) Date of Patent: Aug. 18, 2009

(54) WOUND DRESSING FOR ACCELERATING EPIDERMAL REGENERATION

(75) Inventors: Masato Kurokawa, Kyoto (JP); Hiroaki Nakamura, Tokyo (JP)

(73) Assignee: Sanyo Chemical Industries, Ltd., Kyoto-shi (JP)

( * ) Notice: Subject to any disclaimer, the term of this patent is extended or adjusted under 35 U.S.C. 154(b) by 0 days.

(21) Appl. No.: 10/797,606

(22) Filed: Mar. 11, 2004

(65) Prior Publication Data

US 2005/0202069 A1    Sep. 15, 2005

(51) Int. Cl.
*A61K 38/00* (2006.01)
*A61F 13/02* (2006.01)
*A61F 5/03* (2006.01)

(52) U.S. Cl. .......................... 514/2; 530/300; 604/304; 602/3

(58) Field of Classification Search .................. None
See application file for complete search history.

(56) References Cited

U.S. PATENT DOCUMENTS

| | | | |
|---|---|---|---|
| 5,514,581 A | | 5/1996 | Ferrari et al. |
| 5,916,585 A | * | 6/1999 | Cook et al. ................. 424/426 |
| 6,184,348 B1 | * | 2/2001 | Ferrari et al. ............... 530/350 |
| 6,828,354 B2 | * | 12/2004 | Hahnle et al. ............... 521/187 |

FOREIGN PATENT DOCUMENTS

| | | |
|---|---|---|
| JP | 2003-304868 | 10/2003 |
| JP | 2004-49921 | 2/2004 |
| WO | WO 02/26872 A1 * | 4/2002 |

OTHER PUBLICATIONS

Lin, 1994, Journal of Biomedical Material Research, 28, 329-342.*

* cited by examiner

*Primary Examiner*—Cecilia Tsang
*Assistant Examiner*—Satyanarayana R Gudibande
(74) *Attorney, Agent, or Firm*—Westerman, Hattori, Daniels & Adrian, LLP.

(57) ABSTRACT

The present invention provides a wound dressing capable of accelerating epidermal regeneration.

The present invention relates to
a wound dressing for accelerating epidermal regeneration which comprises
a polypeptide (P) having at least one species of epidermal regeneration-accelerating minimal amino acid sequences (X) selected from the group consisting of the Arg Gly Asp sequence (1), the Ile Lys Val Ala Val sequence (2), and the Tyr Ile Gly Ser Arg sequence (3) and an auxiliary amino acid sequence (Y),
a polyalkylenepolyamine and/or polyarylenepolyamine (A) having a weight average molecular weight of 2,000 to 60,000, and
a sheet (S).

5 Claims, 3 Drawing Sheets

SEQUENCE LISTING

```
<160> NUMBER OF SEQ ID NOS: 49

<210> SEQ ID NO 1
<211> LENGTH: 3
<212> TYPE: PRT
<213> ORGANISM: Homo sapiens

<400> SEQUENCE: 1

Arg Gly Asp
1

<210> SEQ ID NO 2
<211> LENGTH: 5
<212> TYPE: PRT
<213> ORGANISM: Homo sapiens

<400> SEQUENCE: 2

Ile Lys Val Ala Val
1               5

<210> SEQ ID NO 3
<211> LENGTH: 5
<212> TYPE: PRT
<213> ORGANISM: Homo sapiens

<400> SEQUENCE: 3

Tyr Ile Gly Ser Arg
1               5

<210> SEQ ID NO 4
<211> LENGTH: 10
<212> TYPE: PRT
<213> ORGANISM: Artificial Sequence
<220> FEATURE:
<223> OTHER INFORMATION: auxiliary amino acid sequence (Y)

<400> SEQUENCE: 4

Gly Ala Gly Ala Gly Ala Gly Ala Gly Ala
1               5                   10

<210> SEQ ID NO 5
<211> LENGTH: 40
```

```
<212> TYPE: PRT
<213> ORGANISM: Artificial Sequence
<220> FEATURE:
<223> OTHER INFORMATION: auxiliary amino acid sequence (Y)

<400> SEQUENCE: 5

Gly Ala Gly Ala Gly Ala Gly Ala Gly Ala Gly Ala Gly Ala Gly Ala
1               5                   10                  15

Gly Ala Gly Ala Gly Ala Gly Ala Gly Ala Gly Ala Gly Ala Gly Ala
            20                  25                  30

Gly Ala Gly Ala Gly Ala Gly Ala
        35                  40

<210> SEQ ID NO 6
<211> LENGTH: 160
<212> TYPE: PRT
<213> ORGANISM: Artificial Sequence
<220> FEATURE:
<223> OTHER INFORMATION: auxiliary amino acid sequence (Y)

<400> SEQUENCE: 6

Gly Ala Gly Ala Gly Ala Gly Ala Gly Ala Gly Ala Gly Ala Gly Ala
1               5                   10                  15

Gly Ala Gly Ala Gly Ala Gly Ala Gly Ala Gly Ala Gly Ala Gly Ala
            20                  25                  30

Gly Ala Gly Ala Gly Ala Gly Ala Gly Ala Gly Ala Gly Ala Gly Ala
        35                  40                  45

Gly Ala Gly Ala Gly Ala Gly Ala Gly Ala Gly Ala Gly Ala Gly Ala
    50                  55                  60

Gly Ala Gly Ala Gly Ala Gly Ala Gly Ala Gly Ala Gly Ala Gly Ala
65                  70                  75                  80

Gly Ala Gly Ala Gly Ala Gly Ala Gly Ala Gly Ala Gly Ala Gly Ala
                85                  90                  95

Gly Ala Gly Ala Gly Ala Gly Ala Gly Ala Gly Ala Gly Ala Gly Ala
            100                 105                 110

Gly Ala Gly Ala Gly Ala Gly Ala Gly Ala Gly Ala Gly Ala Gly Ala
        115                 120                 125

Gly Ala Gly Ala Gly Ala Gly Ala Gly Ala Gly Ala Gly Ala Gly Ala
    130                 135                 140

Gly Ala Gly Ala Gly Ala Gly Ala Gly Ala Gly Ala Gly Ala Gly Ala
145                 150                 155                 160

<210> SEQ ID NO 7
<211> LENGTH: 12
<212> TYPE: PRT
<213> ORGANISM: Artificial Sequence
<220> FEATURE:
<223> OTHER INFORMATION: auxiliary amino acid sequence (Y)

<400> SEQUENCE: 7

Gly Ala Gly Ala Gly Ser Gly Ala Gly Ala Gly Ser
1               5                   10

<210> SEQ ID NO 8
<211> LENGTH: 54
<212> TYPE: PRT
<213> ORGANISM: Artificial Sequence
<220> FEATURE:
<223> OTHER INFORMATION: auxiliary amino acid sequence (Y)

<400> SEQUENCE: 8
```

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser
    50

<210> SEQ ID NO 9
<211> LENGTH: 180
<212> TYPE: PRT
<213> ORGANISM: Artificial Sequence
<220> FEATURE:
<223> OTHER INFORMATION: auxiliary amino acid sequence (Y)

<400> SEQUENCE: 9

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Gly Ala Gly Ser Gly Ala Gly Ala
    50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser Gly Ala Gly Ala Gly Ser
                85                  90                  95

Gly Ala Gly Ala Gly Ser Gly Ala Gly Ala Gly Ser Gly Ala Gly Ala
                100                 105                 110

Gly Ser Gly Ala Gly Ala Gly Ser Gly Ala Gly Ala Gly Ser Gly Ala
            115                 120                 125

Gly Ala Gly Ser Gly Ala Gly Ala Gly Ser Gly Ala Gly Ala Gly Ser
    130                 135                 140

Gly Ala Gly Ala Gly Ser Gly Ala Gly Ala Gly Ser Gly Ala Gly Ala
145                 150                 155                 160

Gly Ser Gly Ala Gly Ala Gly Ser Gly Ala Gly Ala Gly Ser Gly Ala
                165                 170                 175

Gly Ala Gly Ser
            180

<210> SEQ ID NO 10
<211> LENGTH: 12
<212> TYPE: PRT
<213> ORGANISM: Artificial Sequence
<220> FEATURE:
<223> OTHER INFORMATION: auxiliary amino acid sequence (Y)

<400> SEQUENCE: 10

Gly Ala Gly Ala Gly Tyr Gly Ala Gly Ala Gly Tyr
1               5                   10

<210> SEQ ID NO 11
<211> LENGTH: 54
<212> TYPE: PRT
<213> ORGANISM: Artificial Sequence
<220> FEATURE:
<223> OTHER INFORMATION: auxiliary amino acid sequence (Y)

<400> SEQUENCE: 11

Gly Ala Gly Ala Gly Tyr Gly Ala Gly Ala Gly Tyr Gly Ala Gly Ala
1               5                   10                  15

Gly Tyr Gly Ala Gly Ala Gly Tyr Gly Ala Gly Ala Gly Tyr Gly Ala
                20                  25                  30

Gly Ala Gly Tyr Gly Ala Gly Ala Gly Tyr Gly Ala Gly Ala Gly Tyr
            35                  40                  45

Gly Ala Gly Ala Gly Tyr
        50

<210> SEQ ID NO 12
<211> LENGTH: 180
<212> TYPE: PRT
<213> ORGANISM: Artificial Sequence
<220> FEATURE:
<223> OTHER INFORMATION: auxiliary amino acid sequence (Y)

<400> SEQUENCE: 12

Gly Ala Gly Ala Gly Tyr Gly Ala Gly Ala Gly Tyr Gly Ala Gly Ala
1               5                   10                  15

Gly Tyr Gly Ala Gly Ala Gly Tyr Gly Ala Gly Ala Gly Tyr Gly Ala
                20                  25                  30

Gly Ala Gly Tyr Gly Ala Gly Ala Gly Tyr Gly Ala Gly Ala Gly Tyr
            35                  40                  45

Gly Ala Gly Ala Gly Tyr Gly Ala Gly Ala Gly Tyr Gly Ala Gly Ala
        50                  55                  60

Gly Tyr Gly Ala Gly Ala Gly Tyr Gly Ala Gly Ala Gly Tyr Gly Ala
65                  70                  75                  80

Gly Ala Gly Tyr Gly Ala Gly Ala Gly Tyr Gly Ala Gly Ala Gly Tyr
                85                  90                  95

Gly Ala Gly Ala Gly Tyr Gly Ala Gly Ala Gly Tyr Gly Ala Gly Ala
            100                 105                 110

Gly Tyr Gly Ala Gly Ala Gly Tyr Gly Ala Gly Ala Gly Tyr Gly Ala
        115                 120                 125

Gly Ala Gly Tyr Gly Ala Gly Ala Gly Tyr Gly Ala Gly Ala Gly Tyr
    130                 135                 140

Gly Ala Gly Ala Gly Tyr Gly Ala Gly Ala Gly Tyr Gly Ala Gly Ala
145                 150                 155                 160

Gly Tyr Gly Ala Gly Ala Gly Tyr Gly Ala Gly Ala Gly Tyr Gly Ala
                165                 170                 175

Gly Ala Gly Tyr
            180

<210> SEQ ID NO 13
<211> LENGTH: 12
<212> TYPE: PRT
<213> ORGANISM: Artificial Sequence
<220> FEATURE:
<223> OTHER INFORMATION: auxiliary amino acid sequence (Y)

<400> SEQUENCE: 13

Gly Ala Gly Val Gly Tyr Gly Ala Gly Val Gly Tyr
1               5                   10

<210> SEQ ID NO 14
<211> LENGTH: 54
<212> TYPE: PRT
<213> ORGANISM: Artificial Sequence
<220> FEATURE:

<223> OTHER INFORMATION: auxiliary amino acid sequence (Y)

<400> SEQUENCE: 14

```
Gly Ala Gly Val Gly Tyr Gly Ala Gly Val Gly Tyr Gly Ala Gly Val
1               5                   10                  15
Gly Tyr Gly Ala Gly Val Gly Tyr Gly Ala Gly Val Gly Tyr Gly Ala
            20                  25                  30
Gly Val Gly Tyr Gly Ala Gly Val Gly Tyr Gly Ala Gly Val Gly Tyr
        35                  40                  45
Gly Ala Gly Val Gly Tyr
    50
```

<210> SEQ ID NO 15
<211> LENGTH: 180
<212> TYPE: PRT
<213> ORGANISM: Artificial Sequence
<220> FEATURE:
<223> OTHER INFORMATION: auxiliary amino acid sequence (Y)

<400> SEQUENCE: 15

```
Gly Ala Gly Val Gly Tyr Gly Ala Gly Val Gly Tyr Gly Ala Gly Val
1               5                   10                  15
Gly Tyr Gly Ala Gly Val Gly Tyr Gly Ala Gly Val Gly Tyr Gly Ala
            20                  25                  30
Gly Val Gly Tyr Gly Ala Gly Val Gly Tyr Gly Ala Gly Val Gly Tyr
        35                  40                  45
Gly Ala Gly Val Gly Tyr Gly Ala Gly Val Gly Tyr Gly Ala Gly Val
    50                  55                  60
Gly Tyr Gly Ala Gly Val Gly Tyr Gly Ala Gly Val Gly Tyr Gly Ala
65                  70                  75                  80
Gly Val Gly Tyr Gly Ala Gly Val Gly Tyr Gly Ala Gly Val Gly Tyr
                85                  90                  95
Gly Ala Gly Val Gly Tyr Gly Ala Gly Val Gly Tyr Gly Ala Gly Val
            100                 105                 110
Gly Tyr Gly Ala Gly Val Gly Tyr Gly Ala Gly Val Gly Tyr Gly Ala
        115                 120                 125
Gly Val Gly Tyr Gly Ala Gly Val Gly Tyr Gly Ala Gly Val Gly Tyr
    130                 135                 140
Gly Ala Gly Val Gly Tyr Gly Ala Gly Val Gly Tyr Gly Ala Gly Val
145                 150                 155                 160
Gly Tyr Gly Ala Gly Val Gly Tyr Gly Ala Gly Val Gly Tyr Gly Ala
                165                 170                 175
Gly Val Gly Tyr
            180
```

<210> SEQ ID NO 16
<211> LENGTH: 12
<212> TYPE: PRT
<213> ORGANISM: Artificial Sequence
<220> FEATURE:
<223> OTHER INFORMATION: auxiliary amino acid sequence (Y)

<400> SEQUENCE: 16

```
Gly Ala Gly Tyr Gly Val Gly Ala Gly Tyr Gly Val
1               5                   10
```

<210> SEQ ID NO 17
<211> LENGTH: 54
<212> TYPE: PRT

```
<213> ORGANISM: Artificial Sequence
<220> FEATURE:
<223> OTHER INFORMATION: auxiliary amino acid sequence (Y)

<400> SEQUENCE: 17

Gly Ala Gly Tyr Gly Val Gly Ala Gly Tyr Gly Val Gly Ala Gly Tyr
1               5                   10                  15

Gly Val Gly Ala Gly Tyr Gly Val Gly Ala Gly Tyr Gly Val Gly Ala
            20                  25                  30

Gly Tyr Gly Val Gly Ala Gly Tyr Gly Val Gly Ala Gly Tyr Gly Val
        35                  40                  45

Gly Ala Gly Tyr Gly Val
    50

<210> SEQ ID NO 18
<211> LENGTH: 180
<212> TYPE: PRT
<213> ORGANISM: Artificial Sequence
<220> FEATURE:
<223> OTHER INFORMATION: auxiliary amino acid sequence (Y)

<400> SEQUENCE: 18

Gly Ala Gly Tyr Gly Val Gly Ala Gly Tyr Gly Val Gly Ala Gly Tyr
1               5                   10                  15

Gly Val Gly Ala Gly Tyr Gly Val Gly Ala Gly Tyr Gly Val Gly Ala
            20                  25                  30

Gly Tyr Gly Val Gly Ala Gly Tyr Gly Val Gly Ala Gly Tyr Gly Val
        35                  40                  45

Gly Ala Gly Tyr Gly Val Gly Ala Gly Tyr Gly Val Gly Ala Gly Tyr
    50                  55                  60

Gly Val Gly Ala Gly Tyr Gly Val Gly Ala Gly Tyr Gly Val Gly Ala
65                  70                  75                  80

Gly Tyr Gly Val Gly Ala Gly Tyr Gly Val Gly Ala Gly Tyr Gly Val
            85                  90                  95

Gly Ala Gly Tyr Gly Val Gly Ala Gly Tyr Gly Val Gly Ala Gly Tyr
            100                 105                 110

Gly Val Gly Ala Gly Tyr Gly Val Gly Ala Gly Tyr Gly Val Gly Ala
        115                 120                 125

Gly Tyr Gly Val Gly Ala Gly Tyr Gly Val Gly Ala Gly Tyr Gly Val
    130                 135                 140

Gly Ala Gly Tyr Gly Val Gly Ala Gly Tyr Gly Val Gly Ala Gly Tyr
145                 150                 155                 160

Gly Val Gly Ala Gly Tyr Gly Val Gly Ala Gly Tyr Gly Val Gly Ala
            165                 170                 175

Gly Tyr Gly Val
        180

<210> SEQ ID NO 19
<211> LENGTH: 48
<212> TYPE: PRT
<213> ORGANISM: Artificial Sequence
<220> FEATURE:
<223> OTHER INFORMATION: auxiliary amino acid sequence (Y)

<400> SEQUENCE: 19

Asp Gly Gly Ala Ala Ala Ala Gly Gly Ala Asp Gly Gly Ala
1               5                   10                  15

Ala Ala Ala Ala Gly Gly Ala Asp Gly Gly Ala Ala Ala Ala Ala
            20                  25                  30
```

```
Ala Gly Gly Ala Asp Gly Gly Ala Ala Ala Ala Gly Gly Ala
        35                  40                  45

<210> SEQ ID NO 20
<211> LENGTH: 18
<212> TYPE: PRT
<213> ORGANISM: Artificial Sequence
<220> FEATURE:
<223> OTHER INFORMATION: auxiliary amino acid sequence (Y)

<400> SEQUENCE: 20

Asp Gly Gly Ala Ala Ala Ala Ala Ala Ala Ala Ala Ala Gly
1               5                   10                  15

Gly Ala

<210> SEQ ID NO 21
<211> LENGTH: 72
<212> TYPE: PRT
<213> ORGANISM: Artificial Sequence
<220> FEATURE:
<223> OTHER INFORMATION: auxiliary amino acid sequence (Y)

<400> SEQUENCE: 21

Asp Gly Gly Ala Ala Ala Ala Ala Ala Ala Ala Ala Ala Gly
1               5                   10                  15

Gly Ala Asp Gly Gly Ala Ala Ala Ala Ala Ala Ala Ala Ala
                20                  25                  30

Ala Gly Gly Ala Asp Gly Gly Ala Ala Ala Ala Ala Ala Ala
        35                  40                  45

Ala Ala Ala Gly Gly Ala Asp Gly Gly Ala Ala Ala Ala Ala
    50                  55                  60

Ala Ala Ala Ala Ala Gly Gly Ala
65                  70

<210> SEQ ID NO 22
<211> LENGTH: 10
<212> TYPE: PRT
<213> ORGANISM: Artificial Sequence
<220> FEATURE:
<223> OTHER INFORMATION: auxiliary amino acid sequence (Y)

<400> SEQUENCE: 22

Gly Val Pro Gly Val Gly Val Pro Gly Val
1               5                   10

<210> SEQ ID NO 23
<211> LENGTH: 50
<212> TYPE: PRT
<213> ORGANISM: Artificial Sequence
<220> FEATURE:
<223> OTHER INFORMATION: auxiliary amino acid sequence (Y)

<400> SEQUENCE: 23

Gly Val Pro Gly Val Gly Val Pro Gly Val Gly Val Pro Gly Val Gly
1               5                   10                  15

Val Pro Gly Val Gly Val Pro Gly Val Gly Val Pro Gly Val Gly Val
                20                  25                  30

Pro Gly Val Gly Val Pro Gly Val Gly Val Pro Gly Val Gly Val Pro
        35                  40                  45

Gly Val
    50
```

<210> SEQ ID NO 24
<211> LENGTH: 200
<212> TYPE: PRT
<213> ORGANISM: Artificial Sequence
<220> FEATURE:
<223> OTHER INFORMATION: auxiliary amino acid sequence (Y)

<400> SEQUENCE: 24

```
Gly Val Pro Gly Val Gly Val Pro Gly Val Gly Val Pro Gly Val Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Val Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
                85                  90                  95

Val Pro Gly Val Gly Val Pro Gly Val Gly Val Pro Gly Val Gly Val
            100                 105                 110

Pro Gly Val Gly Val Pro Gly Val Gly Val Pro Gly Val Gly Val Pro
        115                 120                 125

Gly Val Gly Val Pro Gly Val Gly Val Pro Gly Val Gly Val Pro Gly
    130                 135                 140

Val Gly Val Pro Gly Val Gly Val Pro Gly Val Gly Val Pro Gly Val
145                 150                 155                 160

Gly Val Pro Gly Val Gly Val Pro Gly Val Gly Val Pro Gly Val Gly
                165                 170                 175

Val Pro Gly Val Gly Val Pro Gly Val Gly Val Pro Gly Val Gly Val
            180                 185                 190

Pro Gly Val Gly Val Pro Gly Val
        195                 200
```

<210> SEQ ID NO 25
<211> LENGTH: 10
<212> TYPE: PRT
<213> ORGANISM: Artificial Sequence
<220> FEATURE:
<223> OTHER INFORMATION: auxiliary amino acid sequence (Y)

<400> SEQUENCE: 25

```
Gly Gly Gly Gly Gly Gly Gly Gly Gly Gly
1               5                   10
```

<210> SEQ ID NO 26
<211> LENGTH: 40
<212> TYPE: PRT
<213> ORGANISM: Artificial Sequence
<220> FEATURE:
<223> OTHER INFORMATION: auxiliary amino acid sequence (Y)

<400> SEQUENCE: 26

```
Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly
```

-continued

```
                35                  40

<210> SEQ ID NO 27
<211> LENGTH: 160
<212> TYPE: PRT
<213> ORGANISM: Artificial Sequence
<220> FEATURE:
<223> OTHER INFORMATION: auxiliary amino acid sequence (Y)

<400> SEQUENCE: 27

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly Gly
145                 150                 155                 160

<210> SEQ ID NO 28
<211> LENGTH: 10
<212> TYPE: PRT
<213> ORGANISM: Artificial Sequence
<220> FEATURE:
<223> OTHER INFORMATION: auxiliary amino acid sequence (Y)

<400> SEQUENCE: 28

Ala Ala Ala Ala Ala Ala Ala Ala Ala Ala
1               5                   10

<210> SEQ ID NO 29
<211> LENGTH: 40
<212> TYPE: PRT
<213> ORGANISM: Artificial Sequence
<220> FEATURE:
<223> OTHER INFORMATION: auxiliary amino acid sequence (Y)

<400> SEQUENCE: 29

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala Ala Ala Ala Ala
        35                  40

<210> SEQ ID NO 30
<211> LENGTH: 160
<212> TYPE: PRT
<213> ORGANISM: Artificial Sequence
```

<220> FEATURE:
<223> OTHER INFORMATION: auxiliary amino acid sequence (Y)

<400> SEQUENCE: 30

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala Ala Ala Ala Ala Ala Ala Ala Ala Ala Ala Ala Ala
        35                  40                  45

Ala Ala Ala Ala Ala Ala Ala Ala Ala Ala Ala Ala Ala Ala Ala Ala
50                  55                  60

Ala Ala Ala Ala Ala Ala Ala Ala Ala Ala Ala Ala Ala Ala Ala Ala
65                  70                  75                  80

Ala Ala Ala Ala Ala Ala Ala Ala Ala Ala Ala Ala Ala Ala Ala Ala
                85                  90                  95

Ala Ala Ala Ala Ala Ala Ala Ala Ala Ala Ala Ala Ala Ala Ala Ala
            100                 105                 110

Ala Ala Ala Ala Ala Ala Ala Ala Ala Ala Ala Ala Ala Ala Ala Ala
        115                 120                 125

Ala Ala Ala Ala Ala Ala Ala Ala Ala Ala Ala Ala Ala Ala Ala Ala
    130                 135                 140

Ala Ala Ala Ala Ala Ala Ala Ala Ala Ala Ala Ala Ala Ala Ala Ala
145                 150                 155                 160

<210> SEQ ID NO 31
<211> LENGTH: 9
<212> TYPE: PRT
<213> ORGANISM: Artificial Sequence
<220> FEATURE:
<223> OTHER INFORMATION: auxiliary amino acid sequence (Y)

<400> SEQUENCE: 31

Gly Gly Ala Gly Gly Ala Gly Gly Ala
1               5

<210> SEQ ID NO 32
<211> LENGTH: 36
<212> TYPE: PRT
<213> ORGANISM: Artificial Sequence
<220> FEATURE:
<223> OTHER INFORMATION: auxiliary amino acid sequence (Y)

<400> SEQUENCE: 32

Gly Gly Ala Gly Gly Ala Gly Gly Ala Gly Gly Ala Gly Gly Ala Gly
1               5                   10                  15

Gly Ala Gly Gly Ala Gly Gly Ala Gly Gly Ala Gly Gly Ala Gly Gly
            20                  25                  30

Ala Gly Gly Ala
        35

<210> SEQ ID NO 33
<211> LENGTH: 180
<212> TYPE: PRT
<213> ORGANISM: Artificial Sequence
<220> FEATURE:
<223> OTHER INFORMATION: auxiliary amino acid sequence (Y)

<400> SEQUENCE: 33

Gly Gly Ala Gly Gly Ala Gly Gly Ala Gly Gly Ala Gly Gly Ala Gly
1               5                   10                  15

```
Gly Ala Gly Gly Ala Gly Gly Ala Gly Gly Ala Gly Gly
        20                  25                  30
Ala Gly Gly Ala Gly Gly Ala Gly Gly Ala Gly Gly Ala
            35                  40                  45
Gly Gly Ala Gly Gly Ala Gly Gly Ala Gly Gly Ala Gly
        50                  55                  60
Gly Ala Gly Gly Ala Gly Gly Ala Gly Gly Ala Gly Gly
65                  70                  75                  80
Ala Gly Gly Ala Gly Gly Ala Gly Gly Ala Gly Gly Ala
            85                  90                  95
Gly Gly Ala Gly Gly Ala Gly Gly Ala Gly Gly Ala Gly
        100                 105                 110
Gly Ala Gly Gly Ala Gly Gly Ala Gly Gly Ala Gly Gly
            115                 120                 125
Ala Gly Gly Ala Gly Gly Ala Gly Gly Ala Gly Gly Ala
    130                 135                 140
Gly Gly Ala Gly Gly Ala Gly Gly Ala Gly Gly Ala Gly
145                 150                 155                 160
Gly Ala Gly Gly Ala Gly Gly Ala Gly Gly Ala Gly Gly
            165                 170                 175
Ala Gly Gly Ala
        180

<210> SEQ ID NO 34
<211> LENGTH: 10
<212> TYPE: PRT
<213> ORGANISM: Artificial Sequence
<220> FEATURE:
<223> OTHER INFORMATION: auxiliary amino acid sequence (Y)

<400> SEQUENCE: 34

Gly Val Gly Val Pro Gly Val Gly Val Pro
1               5                   10

<210> SEQ ID NO 35
<211> LENGTH: 50
<212> TYPE: PRT
<213> ORGANISM: Artificial Sequence
<220> FEATURE:
<223> OTHER INFORMATION: auxiliary amino acid sequence (Y)

<400> SEQUENCE: 35

Gly Val Gly Val Pro Gly Val Gly Val Pro Gly Val Gly Val Pro Gly
1               5                   10                  15
Val Gly Val Pro Gly Val Gly Val Pro Gly Val Gly Val Pro Gly Val
            20                  25                  30
Gly Val Pro Gly Val Gly Val Pro Gly Val Gly Val Pro Gly Val Gly
        35                  40                  45
Val Pro
    50

<210> SEQ ID NO 36
<211> LENGTH: 200
<212> TYPE: PRT
<213> ORGANISM: Artificial Sequence
<220> FEATURE:
<223> OTHER INFORMATION: auxiliary amino acid sequence (Y)

<400> SEQUENCE: 36
```

```
Gly Val Gly Val Pro Gly Val Gly Val Pro Gly Val Gly Val Pro Gly
1               5                   10                  15
Val Gly Val Pro Gly Val Gly Val Pro Gly Val Gly Val Pro Gly Val
                20                  25                  30
Gly Val Pro Gly Val Gly Val Pro Gly Val Gly Val Pro Gly Val Gly
            35                  40                  45
Val Pro Gly Val Gly Val Pro Gly Val Gly Val Pro Gly Val Gly Val
        50                  55                  60
Pro Gly Val Gly Val Pro Gly Val Gly Val Pro Gly Val Gly Val Pro
65                  70                  75                  80
Gly Val Gly Val Pro Gly Val Gly Val Pro Gly Val Gly Val Pro Gly
                85                  90                  95
Val Gly Val Pro Gly Val Gly Val Pro Gly Val Gly Val Pro Gly Val
                100                 105                 110
Gly Val Pro Gly Val Gly Val Pro Gly Val Gly Val Pro Gly Val Gly
            115                 120                 125
Val Pro Gly Val Gly Val Pro Gly Val Gly Val Pro Gly Val Gly Val
        130                 135                 140
Pro Gly Val Gly Val Pro Gly Val Gly Val Pro Gly Val Gly Val Pro
145                 150                 155                 160
Gly Val Gly Val Pro Gly Val Gly Val Pro Gly Val Gly Val Pro Gly
                165                 170                 175
Val Gly Val Pro Gly Val Gly Val Pro Gly Val Gly Val Pro Gly Val
                180                 185                 190
Gly Val Pro Gly Val Gly Val Pro
            195                 200

<210> SEQ ID NO 37
<211> LENGTH: 9
<212> TYPE: PRT
<213> ORGANISM: Artificial Sequence
<220> FEATURE:
<223> OTHER INFORMATION: auxiliary amino acid sequence (Y)

<400> SEQUENCE: 37

Gly Pro Pro Gly Pro Pro Gly Pro Pro
1               5

<210> SEQ ID NO 38
<211> LENGTH: 36
<212> TYPE: PRT
<213> ORGANISM: Artificial Sequence
<220> FEATURE:
<223> OTHER INFORMATION: auxiliary amino acid sequence (Y)

<400> SEQUENCE: 38

Gly Pro Pro Gly Pro Pro Gly Pro Pro Gly Pro Pro Gly Pro Pro Gly
1               5                   10                  15
Pro Pro Gly Pro Pro Gly Pro Pro Gly Pro Pro Gly Pro Pro Gly Pro
                20                  25                  30
Pro Gly Pro Pro
        35

<210> SEQ ID NO 39
<211> LENGTH: 180
<212> TYPE: PRT
<213> ORGANISM: Artificial Sequence
<220> FEATURE:
<223> OTHER INFORMATION: auxiliary amino acid sequence (Y)
```

```
<400> SEQUENCE: 39

Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro Gly Pro
            20                  25                  30

Pro Gly Pro Pro Gly Pro Pro Gly Pro Pro Gly Pro Pro Gly Pro Pro
        35                  40                  45

Gly Pro Pro Gly Pro Pro Gly Pro Pro Gly Pro Pro Gly Pro Pro Gly
    50                  55                  60

Pro Pro Gly Pro Pro Gly Pro Pro Gly Pro Pro Gly Pro Pro Gly Pro
65                  70                  75                  80

Pro Gly Pro Pro Gly Pro Pro Gly Pro Pro Gly Pro Pro Gly Pro Pro
            85                  90                  95

Gly Pro Pro Gly Pro Pro Gly Pro Pro Gly Pro Pro Gly Pro Pro Gly
            100                 105                 110

Pro Pro Gly Pro Pro Gly Pro Pro Gly Pro Pro Gly Pro Pro Gly Pro
            115                 120                 125

Pro Gly Pro Pro Gly Pro Pro Gly Pro Pro Gly Pro Pro Gly Pro Pro
        130                 135                 140

Gly Pro Pro Gly Pro Pro Gly Pro Pro Gly Pro Pro Gly Pro Pro Gly
145                 150                 155                 160

Pro Pro Gly Pro Pro Gly Pro Pro Gly Pro Pro Gly Pro Pro Gly Pro
            165                 170                 175

Pro Gly Pro Pro
        180

<210> SEQ ID NO 40
<211> LENGTH: 9
<212> TYPE: PRT
<213> ORGANISM: Artificial Sequence
<220> FEATURE:
<223> OTHER INFORMATION: auxiliary amino acid sequence (Y)

<400> SEQUENCE: 40

Gly Ala Gln Gly Pro Ala Gly Pro Gly
1               5

<210> SEQ ID NO 41
<211> LENGTH: 45
<212> TYPE: PRT
<213> ORGANISM: Artificial Sequence
<220> FEATURE:
<223> OTHER INFORMATION: auxiliary amino acid sequence (Y)

<400> SEQUENCE: 41

Gly Ala Gln Gly Pro Ala Gly Pro Gly Gly Ala Gln Gly Pro Ala Gly
1               5                   10                  15

Pro Gly Gly Ala Gln Gly Pro Ala Gly Pro Gly Gly Ala Gln Gly Pro
            20                  25                  30

Ala Gly Pro Gly Gly Ala Gln Gly Pro Ala Gly Pro Gly
        35                  40                  45

<210> SEQ ID NO 42
<211> LENGTH: 180
<212> TYPE: PRT
<213> ORGANISM: Artificial Sequence
<220> FEATURE:
<223> OTHER INFORMATION: auxiliary amino acid sequence (Y)

<400> SEQUENCE: 42
```

```
Gly Ala Gln Gly Pro Ala Gly Pro Gly Gly Ala Gln Gly Pro Ala Gly
1               5                   10                  15

Pro Gly Gly Ala Gln Gly Pro Ala Gly Pro Gly Gly Ala Gln Gly Pro
                20                  25                  30

Ala Gly Pro Gly Gly Ala Gln Gly Pro Ala Gly Pro Gly Gly Ala Gln
            35                  40                  45

Gly Pro Ala Gly Pro Gly Gly Ala Gln Gly Pro Ala Gly Pro Gly Gly
        50                  55                  60

Ala Gln Gly Pro Ala Gly Pro Gly Gly Ala Gln Gly Pro Ala Gly Pro
65                  70                  75                  80

Gly Gly Ala Gln Gly Pro Ala Gly Pro Gly Gly Ala Gln Gly Pro Ala
                85                  90                  95

Gly Pro Gly Gly Ala Gln Gly Pro Ala Gly Pro Gly Gly Ala Gln Gly
            100                 105                 110

Pro Ala Gly Pro Gly Gly Ala Gln Gly Pro Ala Gly Pro Gly Gly Ala
        115                 120                 125

Gln Gly Pro Ala Gly Pro Gly Gly Ala Gln Gly Pro Ala Gly Pro Gly
    130                 135                 140

Gly Ala Gln Gly Pro Ala Gly Pro Gly Gly Ala Gln Gly Pro Ala Gly
145                 150                 155                 160

Pro Gly Gly Ala Gln Gly Pro Ala Gly Pro Gly Gly Ala Gln Gly Pro
                165                 170                 175

Ala Gly Pro Gly
            180

<210> SEQ ID NO 43
<211> LENGTH: 15
<212> TYPE: PRT
<213> ORGANISM: Artificial Sequence
<220> FEATURE:
<223> OTHER INFORMATION: auxiliary amino acid sequence (Y)

<400> SEQUENCE: 43

Gly Ala Pro Gly Ala Pro Gly Ser Gln Gly Ala Pro Gly Leu Gln
1               5                   10                  15

<210> SEQ ID NO 44
<211> LENGTH: 60
<212> TYPE: PRT
<213> ORGANISM: Artificial Sequence
<220> FEATURE:
<223> OTHER INFORMATION: auxiliary amino acid sequence (Y)

<400> SEQUENCE: 44

Gly Ala Pro Gly Ala Pro Gly Ser Gln Gly Ala Pro Gly Leu Gln Gly
1               5                   10                  15

Ala Pro Gly Ala Pro Gly Ser Gln Gly Ala Pro Gly Leu Gln Gly Ala
            20                  25                  30

Pro Gly Ala Pro Gly Ser Gln Gly Ala Pro Gly Leu Gln Gly Ala Pro
        35                  40                  45

Gly Ala Pro Gly Ser Gln Gly Ala Pro Gly Leu Gln
    50                  55                  60

<210> SEQ ID NO 45
<211> LENGTH: 180
<212> TYPE: PRT
<213> ORGANISM: Artificial Sequence
<220> FEATURE:
<223> OTHER INFORMATION: auxiliary amino acid sequence (Y)
```

-continued

```
<400> SEQUENCE: 45

Gly Ala Pro Gly Ala Pro Gly Ser Gln Gly Ala Pro Gly Leu Gln Gly
1               5                   10                  15

Ala Pro Gly Ala Pro Gly Ser Gln Gly Ala Pro Gly Leu Gln Gly Ala
                20                  25                  30

Pro Gly Ala Pro Gly Ser Gln Gly Ala Pro Gly Leu Gln Gly Ala Pro
            35                  40                  45

Gly Ala Pro Gly Ser Gln Gly Ala Pro Gly Leu Gln Gly Ala Pro Gly
        50                  55                  60

Ala Pro Gly Ser Gln Gly Ala Pro Gly Leu Gln Gly Ala Pro Gly Ala
65                  70                  75                  80

Pro Gly Ser Gln Gly Ala Pro Gly Leu Gln Gly Ala Pro Gly Ala Pro
                85                  90                  95

Gly Ser Gln Gly Ala Pro Gly Leu Gln Gly Ala Pro Gly Ala Pro Gly
                100                 105                 110

Ser Gln Gly Ala Pro Gly Leu Gln Gly Ala Pro Gly Ala Pro Gly Ser
            115                 120                 125

Gln Gly Ala Pro Gly Leu Gln Gly Ala Pro Gly Ala Pro Gly Ser Gln
        130                 135                 140

Gly Ala Pro Gly Leu Gln Gly Ala Pro Gly Ala Pro Gly Ser Gln Gly
145                 150                 155                 160

Ala Pro Gly Leu Gln Gly Ala Pro Gly Ala Pro Gly Ser Gln Gly Ala
                165                 170                 175

Pro Gly Leu Gln
            180

<210> SEQ ID NO 46
<211> LENGTH: 15
<212> TYPE: PRT
<213> ORGANISM: Artificial Sequence
<220> FEATURE:
<223> OTHER INFORMATION: auxiliary amino acid sequence (Y)

<400> SEQUENCE: 46

Gly Ala Pro Gly Thr Pro Gly Pro Gln Gly Leu Pro Gly Ser Pro
1               5                   10                  15

<210> SEQ ID NO 47
<211> LENGTH: 60
<212> TYPE: PRT
<213> ORGANISM: Artificial Sequence
<220> FEATURE:
<223> OTHER INFORMATION: auxiliary amino acid sequence (Y)

<400> SEQUENCE: 47

Gly Ala Pro Gly Thr Pro Gly Pro Gln Gly Leu Pro Gly Ser Pro Gly
1               5                   10                  15

Ala Pro Gly Thr Pro Gly Pro Gln Gly Leu Pro Gly Ser Pro Gly Ala
                20                  25                  30

Pro Gly Thr Pro Gly Pro Gln Gly Leu Pro Gly Ser Pro Gly Ala Pro
            35                  40                  45

Gly Thr Pro Gly Pro Gln Gly Leu Pro Gly Ser Pro
        50                  55                  60

<210> SEQ ID NO 48
<211> LENGTH: 180
<212> TYPE: PRT
<213> ORGANISM: Artificial Sequence
```

-continued

```
<220> FEATURE:
<223> OTHER INFORMATION: auxiliary amino acid sequence (Y)

<400> SEQUENCE: 48

Gly Ala Pro Gly Thr Pro Gly Pro Gln Gly Leu Pro Gly Ser Pro Gly
1               5                   10                  15

Ala Pro Gly Thr Pro Gly Pro Gln Gly Leu Pro Gly Ser Pro Gly Ala
            20                  25                  30

Pro Gly Thr Pro Gly Pro Gln Gly Leu Pro Gly Ser Pro Gly Ala Pro
        35                  40                  45

Gly Thr Pro Gly Pro Gln Gly Leu Pro Gly Ser Pro Gly Ala Pro Gly
    50                  55                  60

Thr Pro Gly Pro Gln Gly Leu Pro Gly Ser Pro Gly Ala Pro Gly Thr
65                  70                  75                  80

Pro Gly Pro Gln Gly Leu Pro Gly Ser Pro Gly Ala Pro Gly Thr Pro
                85                  90                  95

Gly Pro Gln Gly Leu Pro Gly Ser Pro Gly Ala Pro Gly Thr Pro Gly
            100                 105                 110

Pro Gln Gly Leu Pro Gly Ser Pro Gly Ala Pro Gly Thr Pro Gly Pro
        115                 120                 125

Gln Gly Leu Pro Gly Ser Pro Gly Ala Pro Gly Thr Pro Gly Pro Gln
    130                 135                 140

Gly Leu Pro Gly Ser Pro Gly Ala Pro Gly Thr Pro Gly Pro Gln Gly
145                 150                 155                 160

Leu Pro Gly Ser Pro Gly Ala Pro Gly Thr Pro Gly Pro Gln Gly Leu
                165                 170                 175

Pro Gly Ser Pro
            180

<210> SEQ ID NO 49
<211> LENGTH: 30
<212> TYPE: PRT
<213> ORGANISM: Artificial Sequence
<220> FEATURE:
<223> OTHER INFORMATION: auxiliary amino acid sequence (Y)

<400> SEQUENCE: 49

Gly Val Pro Gly Val Gly Val Pro Gly Val Gly Gly Ala Gly Ala
1               5                   10                  15

Gly Ser Gly Ala Gly Ala Gly Ser Gly Ala Gly Ala Gly Ser
            20                  25                  30
```

WOUND DRESSING FOR ACCELERATING EPIDERMAL REGENERATION

TECHNICAL FIELD

The present invention relates to a wound dressing for accelerating epidermal regeneration. More particularly, the invention relates to a wound dressing which accelerates epidermal regeneration and, thus, contributes to the healing of a skin wound.

BACKGROUND ART

Wound dressings inclusive of an alginate {Kaltostat (product of Bristol-Myers Squibb Co.)}, chitin {Beschitin (product of Unitika Ltd.)}, a hydrocolloid {DuoActive (product of Bristol-Myers Squibb Co.)}, a polyurethane {Tegaderm (product of 3M Health Care Ltd.), Bioclusive (product of Johnson & Johnson Medical Co.)}, and the like, are known (The Current Status and Future Outlook of Medical Plastics, 2000, published by Fuji Chimera Research Institute, Inc., 2000). On the other hand, artificial dermis preparations of collagen {Terudermis (product of Terumo corporation), Pelnac (product of Gunze Ltd.)}, and the like, are also known (The Current Status and Future Outlook of Medical Plastics, 2000, published by Fuji Chimera Research Institute, Inc., 2000).

SUMMARY OF THE INVENTION

The conventional wound dressings are conducive to spontaneous healing of a wound by forming a moist environment on the wounded skin surface and/or preventing infiltration of adventitious infective bacteria but has no action to accelerate regeneration of the wounded skin. In cases where spontaneous healing of the wounded epidermis can hardly be expected, the conventional wound dressing has the drawback that the formation of keloids and cicatrices such as hypertrophic scar and cicatricial contracture on the skin is inevitable. To prevent such cicatrices, a full-thickness skin or partial-thickness skin (epidermal) graft is taken from the patient's own inguinal region (groin), clavicular region or the like, and transplanted. Thus, with the conventional wound dressing alone, it is frequently the case that the wound cannot be adequately cured.

Meanwhile, the conventional artificial dermis is effective in accelerating dermal regeneration, when applied to the defected skin area, but has proven incapable of accelerating epidermal regeneration. Therefore, the conventional artificial dermis has the drawback that the formation of keloids and cicatrices such as hypertrophic scar and cicatricial contracture on the skin is inevitable. To prevent such cicatrices, a partial-thickness skin (epidermal) graft taken from the patient's own inguinal region (groin), clavicular region or the like must be transplanted to the wounded area after successful dermal regeneration. Therefore, with the conventional artificial dermis alone, it is frequently the case that wounds cannot be adequately cured.

The object of the present invention is to provide a wound dressing capable of accelerating epidermal regeneration.

The wound dressing for accelerating epidermal regeneration according to the invention is characterized in that it comprises a polypeptide (P) having at least one species of epidermal regeneration-accelerating minimal amino acid sequences (X) selected from the group consisting of the Arg Gly Asp sequence (1), the Ile Lys Val Ala Val sequence (2), and the Tyr Ile Gly Ser Arg sequence (3) and an auxiliary amino acid sequence (Y), a polyalkylenepolyamine and/or polyarylenepolyamine (A) having a weight average molecular weight of 2,000 to 60,000, and a sheet (S).

The present invention is further directed to a method for epidermal regeneration treatment which comprises using said wound dressing.

DETAILED DESCRIPTION OF THE INVENTION

Figure 1:
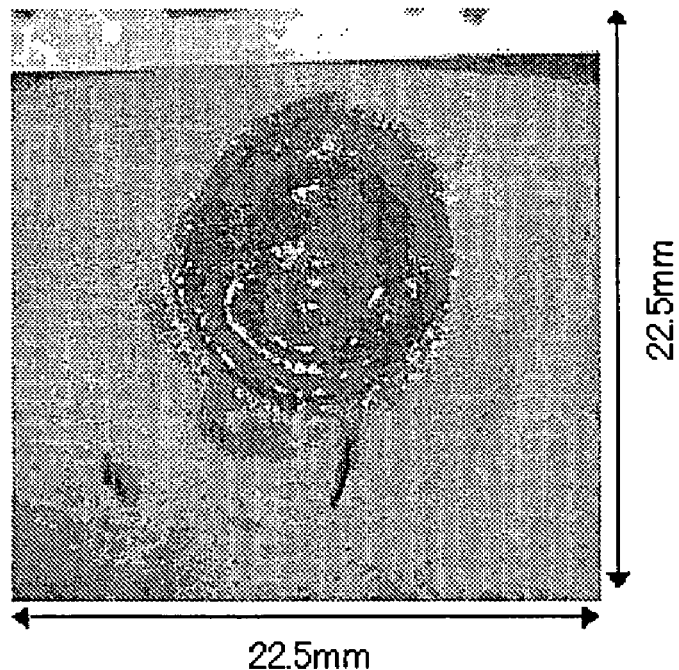
FIG. 1 is a photograph showing the status of wound healing in DM mice on day 7 by using the wound dressing of Example 1.

The epidermal regeneration-accelerating minimal amino acid sequence (X) mentioned above is at least one species selected from the group consisting of the Arg Gly Asp sequence (1), the Ile Lys Val Ala Val sequence (2), and the Tyr Ile Gly Ser Arg sequence (3), and from the standpoint of epidermal regeneration accelerating effect and other reasons, is preferably the Arg Gly Asp sequence (1) and/or the Ile Lys Val Ala Val sequence (2), most preferably the Arg Gly Asp sequence (1). It should be understood that the Arg Gly Asp sequence (1) is the amino acid sequence defined under SEQ ID NO:1.

From the standpoint of epidermal regeneration accelerating effect and other reasons, the polypeptide (P) should have the epidermal regeneration-accelerating minimal amino acid sequence (X) in the number of preferably 3 to 50, more preferably 4 to 35, most preferably 5 to 20, in each molecule. Optionally, this polypeptide (P) may have two or more different species of minimal amino acid sequence (X).

As the auxiliary amino acid sequence (Y), amino acid sequences other than the minimal amino acid sequence (X) can be used and from the standpoint of heat resistance of the polypeptide (P) and other reasons, a sequence containing Gly and/or Ala is preferred. Thus, as (Y), there can be mentioned a sequence containing the (Gly Ala)a sequence, (Gly Ala Gly Ala Gly Ser)b sequence, (Gly Ala Gly Ala Gly Tyr)c sequence, (Gly Ala Gly Val Gly Tyr)d sequence, (Gly Ala Gly Tyr Gly Val)e sequence, {Asp Gly Gly (Ala)f Gly Gly Ala}g sequence, (Gly Val Pro Gly Val)h sequence, (Gly)i sequence, (Ala)j sequence, (Gly Gly Ala)k sequence, (Gly Val Gly Val Pro)m sequence, (Gly Pro Pro)n sequence, (Gly Ala Gln Gly Pro Ala Gly Pro Gly)o sequence, (Gly Ala Pro Gly Ala Pro Gly Ser Gln Gly Ala Pro Gly Leu Gln)p sequence and/or (Gly Ala Pro Gly Thr Pro Gly Pro Gln Gly Leu Pro Gly Ser Pro)q sequence, and the like. Among these, a sequence containing the (Gly Ala)a sequence, (Gly Ala Gly Ala Gly Ser)b sequence, (Gly Ala Gly Ala Gly Tyr)c sequence, (Gly Ala Gly Val Gly Tyr)d sequence, (Gly Ala Gly Tyr Gly Val)e sequence, {Asp Gly Gly (Ala)f Gly Gly Ala}g sequence, (Gly Val Pro Gly Val)h sequence, (Gly Val Gly Val Pro)m sequence and/or (Gly Pro Pro)n sequence is preferred; a sequence containing the (Gly Ala Gly Ala Gly Ser)b sequence, (Gly Val Pro Gly Val)h sequence, (Gly Val Gly Val Pro)m sequence and/or (Gly Pro Pro)n sequence is more preferred, and a sequence containing the (Gly Ala Gly Ala Gly Ser)b sequence is most preferred.

Referring to the above sequences, a represents an integer of 5 to 100; b, c, d, and e each represents an integer of 2 to 33; f represents an integer of 1 to 194; g represents an integer of 1 to {200/(6+f)} with any fraction omitted; h represents an integer of 2 to 40; i and j each represents an integer of 10 to 200; k represents an integer of 3 to 66; m represents an integer of 2 to 40; n represents an integer of 3 to 66; o represents an integer of 1 to 22; and p and q each represents an integer of 1 to 13.

Examples of the sequence containing the (Gly Ala)a sequence to be mentioned are the amino acid sequences defined under SEQ ID NOS:(4) to (6), and the like.

Examples of the sequence containing the (Gly Ala Gly Ala Gly Ser)b sequence to be mentioned are the amino acid sequences defined under SEQ ID NOS:(7) to (9), and the like.

Examples of the sequence containing the (Gly Ala Gly Ala Gly Tyr)c sequence to be mentioned are the amino acid sequences defined under SEQ ID NOS:(10) to (12), and the like.

Examples of the sequence containing the (Gly Ala Gly Vla Gly Tyr)d sequence to be mentioned are the amino acid sequences defined under SEQ ID NOS:(13) to (15), and the like.

Examples of the sequence containing the (Gly Ala Gly Tyr Gly Val)e sequence to be mentioned are the amino acid sequences defined under SEQ ID NOS:(16) to (18), and the like.

Examples of the sequence containing the {Asp Gly Gly (Ala)f Gly Gly Ala}g sequence to be mentioned are the amino acid sequences defined under SEQ ID NOS:(19) to (21), and the like.

Examples of the sequence containing the (Gly Val Pro Gly Val)h sequence to be mentioned are the amino acid sequences defined under SEQ ID NOS:(22) to (24), and the like.

Examples of the sequence containing the (Gly)i sequence to be mentioned are the amino acid sequences defined under SEQ ID NOS:(25) to (27), and the like.

Examples of the sequence containing the (Ala)j sequence to be mentioned are the amino acid sequences defined under SEQ ID NOS:(28) to (30), and the like.

Examples of the sequence containing the (Gly Gly Ala)k sequence to be mentioned are the amino acid sequences defined under SEQ ID NOS:(31) to (33), and the like.

Examples of the sequence containing the (Gly Val Gly Val Pro)m sequence to be mentioned are the amino acid sequences defined under SEQ ID NOS:(34) to (36), and the like.

Examples of the sequence containing the (Gly Pro Pro)n sequence to be mentioned are the amino acid sequences defined under SEQ ID NOS:(37) to (39), and the like.

Examples of the sequence containing the (Gly Ala Gln Gly Pro Ala Gly Pro Gly)o sequence to be mentioned are the amino acid sequences defined under SEQ ID NOS:(40) to (42) and the like.

Examples of the sequence containing the (Gly Ala Pro Gly Ala Pro Gly Ser Gln Gly Ala Pro Gly Leu Gln)p sequence to be mentioned are the amino acid sequences defined under SEQ ID NOS:(43) to (45), and the like.

Examples of the sequence containing the (Gly Ala Pro Gly Thr Pro Gly Pro Gln Gly Leu Pro Gly Ser Pro)q sequence to be mentioned are the amino acid sequences defined under SEQ ID NOS:(46) to (48), and the like.

The auxiliary amino acid sequence (Y) preferably contains glycine (Gly) and/or alanine (Ala). When it contains glycine (Gly) and/or alanine (Ala), the total percentage (%) of (Gly) and/or (Ala) based on the total number of amino acids in the auxiliary amino acid sequence (Y) is preferably 10 to 100, more preferably 20 to 95, particularly preferably 30 to 90, most preferably 40 to 85. Thus, the lower limit of the total percentage (%) of (Gly) and (Ala) based on the total number of amino acids in (Y) is preferably 10, more preferably 20, particularly preferably 30, most preferably 40. Similarly, the upper limit is preferably 100, more preferably 95, particularly preferably 90, most preferably 85. Within this range, heat resistance of the polypeptide (P) is further improved.

In cases where both glycine (Gly) and alanine (Ala) are contained, their numerical ratio, i.e. (Gly/Ala), is preferably 0.03 to 40, more preferably 0.08 to 13, particularly preferably 0.2 to 5. Thus, in such cases, the lower limit of the numerical ratio of glycine (Gly) to alanine (Ala), i.e. (Gly/Ala), is preferably 0.03, more preferably 0.08, particularly preferably 0.2. Similarly the upper limit is preferably 40, more preferably 13, particularly preferably 5. Within this range, heat resistance of the polypeptide (P) is further improved.

From the standpoint of heat resistance of the polypeptide (P) and other reasons, the polypeptide (P) should have the auxiliary amino acid sequence (Y) in the number of preferably 2 to 51, more preferably 3 to 35, particularly preferably 4 to 20, in each molecule. Furthermore, the polypeptide (P) may optionally have two or more different species of the auxiliary amino acid sequence (Y).

The polypeptide (P) may have a branched chain, be partially crosslinked, and/or have a ring structure. However, the polypeptide (P) is preferably not crosslinked and more preferably has an uncrosslinked linear structure, particularly preferably an uncrosslinked and ring-free linear structure. In this connection, as said linear structure, there can be mentioned a β-structure (a secondary structure such that a linear peptide is pleated to form parallel chains with hydrogen bonds therebetween).

From the standpoint of epidermal regeneration accelerating effect and heat resistance of the polypeptide (P) and other reasons, the polypeptide (P) preferably has a structure such that the minimal amino acid sequence (X) and the auxiliary amino acid sequence (Y) are chemically bonded to each other in an alternating fashion. In this connection, from the standpoint of epidermal regeneration accelerating effect and other reasons, the number of the repeating unit (X—Y) consisting of the minimal amino acid sequence (X) and the auxiliary amino acid sequence (Y) is preferably 2 to 50, more preferably 2 to 40, particularly preferably 3 to 30, most preferably 4 to 20, in each molecule.

The weight average molecular weight (Mw) of the polypeptide (P) is preferably 1,000 to 1,000,000, more preferably 2,000 to 700,000, particularly preferably 3,000 to 400,000, most preferably 4,000 to 200,000. Thus, the lower limit of (Mw) of the polypeptide (P) is preferably 1,000, more preferably 2,000, particularly preferably 3,000, most preferably 4,000 and similarly the upper limit is preferably 1,000,000, more preferably 700,000, particularly preferably 400,000, most preferably 200,000.

In the context of the present invention, the weight average molecular weight (Mw) of the polypeptide (P) is determined by the method which comprises fractionating a sample (e.g. polypeptide and the like) by SDS-PAGE (SDS-polyacrylamide gel electrophoresis) and comparing the migration distance thereof with that of the standard substance.

As the polypeptide (P), the following polypeptides are preferred.

(I) Polypeptides having the Arg Gly Asp sequence (1) as the minimal amino acid sequence (X):
the polypeptide having the sequence (1) in the number of 13 and, as the auxiliary amino acid sequence (Y), the (Gly Ala Gly Ala Gly Ser)$_9$ sequence (8) (y1) in the number of 13, which sequences are chemically bonded to each other in an alternating fashion, and having a Mw of about 110,000 ("ProNectin F", ProNectin is a registered trademark (Japan and USA), product of Sanyo Chemical Industries, Ltd. (the same applies hereinafter));

the polypeptide having the sequence (1) in the number of 5 and, as the auxiliary amino acid sequence (Y), the (Gly Ala Gly Ala Gly Ser)$_3$ sequence (7) (y2) in the number of 5, which are chemically bonded to each other in an alternating fashion, and having a Mw of about 20,000 ("ProNectin F2");

the polypeptide having the sequence (1) in the number of 3 and, as the auxiliary amino sequence (Y), the (Gly Val Pro Gly Val)$_2$ Gly Gly (Gly Ala Gly Ala Gly Ser)$_3$ sequence (49) (y3) in the number of 3, which are chemically bonded to each other in an alternating fashion, and having a Mw of about 10,000 ("ProNectin F3"); and the like.

(II) Polypeptides having the Ile Lys Val Ala Val sequence (2) as the minimal amino acid sequence (X):

"ProNectin L", "ProNectin L2" and "ProNectin L3", which are obtainable by substituting the Ile Lys Val Ala Val sequence (2) for the Arg Gly Asp sequence (1) of ProNectin F, ProNectin F2 and ProNectin F3, and the like.

(III) Polypeptides having the Tyr Ile Gly Ser Arg sequence (3) as the minimal amino acid sequence (X):

"ProNectin Y", "ProNectin Y2" and "ProNectin y3" which are obtainable by substituting the Tyr Ile Gly Ser Arg sequence (3) for the Arg Gly Asp sequence (1) of ProNectin F, ProNectin F2 and ProNectin F3, and the like.

As the polypeptide (P), either one species or two or more different species can be used.

The polypeptide (P) can be easily produced artificially by organic synthesis (enzymatic synthesis, solid-phase synthesis, liquid-phase synthesis and the like), recombinant DNA and other technologies. Referring to said organic synthesis, the method described in Seikagaku Jikken Koza (Lectures on Biochemical Experiments) 1, Protein Chemistry IV (Jul. 1, 1981, edited by the Japanese Biochemical Society, published by Tokyo Kagaku Dojin K.K.) or Seikagaku Jikken Koza (Lectures on Biochemical Experiments)—continued—2, Protein Chemistry (II) (May 20, 1986, edited by the Japanese Biochemical Society, published by Tokyo Kagaku Dojin K.K.), and the like, can be used. Referring to the recombinant DNA technology, the method described in Japanese Patent No. 3338441 (corresponding to U.S. Pat. No. 5,514,581; the disclosure thereof is incorporated in this specification by reference), and the like, can be used. From the standpoint that the polypeptide (P) can be produced on a high production scale at low cost, and from other reasons, the recombinant DNA technology is preferred.

The wound dressing of the present invention comprises a polyalkylenepolyamine and/or polyarylenepolyamine having a weight average molecular weight of 2,000 to 60,000 (A) (hereinafter referred to briefly as polyamine (A)) in combination with the polypeptide (P). In the present invention, the polyamine (A) is an essential component necessary for expression of an epidermal regeneration accelerating effect. With any compound other than the polyamine (A), for example poly-L-lysine, dimethylaminoethyl methacrylate polymer (DEA polymer), quaternized DEA polymer or the like, the epidermal regeneration accelerating effect cannot be obtained at all or in any significant measure.

Examples of the polyalkylenepolyamine to be mentioned are compounds having a plurality of alkylene groups and a plurality of at least one species selected from the group consisting of primary through tertiary amino and ammonio groups, and the like.

Examples of the polyarylenepolyamine to be mentioned are compounds having a plurality of arylene groups and a plurality of at least one species selected from the group consisting of primary through tertiary amino and ammonio groups, and the like.

The polyalkylenepolyamine may be such that some of its alkylene groups have been replaced by arylene groups. Similarly, the polyarylenepolyamine may be such that some of its arylene groups have been replaced by alkylene groups.

The polyamine (A) may be linear or branched. Examples of the branched polyamine to be mentioned are polymers having the following chemical structure:

$$\cdots\text{—NH—R—N—R—NH—}\cdots$$
$$|$$
$$\text{R—NH—R—}\cdots$$
$$\cdots\text{—N—R—N—R—N}\cdots$$
$$|\quad\quad|$$
$$\cdots\text{N—R}\quad\text{R—N—R—N—R—}\cdots$$
$$|\quad\quad|$$
$$\cdots\text{N—R}\quad\text{R—N}\cdots$$

(wherein R represents an alkylene or arylene group which may be the same or different over its plurality of occurrences).

Examples of the linear polyamine to be mentioned are polymers which may be represented by the following chemical formula:

$$R'_2N\text{—}(R\text{—}NR'\text{—})_nR'$$

(wherein R represents an alkylene or arylene group which may be the same or different over its n occurrences; R' represents a hydrogen atom or an alkyl group containing 1 to 4 carbon atoms; n represents a number insuring that the weight average molecular weight of the polymer will be 2,000 to 60,000).

Examples of the alkylene group of the polyamine (A) to be mentioned are alkylene groups containing 2 to 6 carbon atoms (ethylene, propylene, iso-propylene, butylene, hexylene and the like), and the like.

Examples of the arylene group to be mentioned are arylene groups containing 4 to 8 carbon atoms (furandiyl, phenylene, toluenediyl, xylenediyl and the like), and the like.

From the standpoint of epidermal regeneration accelerating effect and other reasons, preferred among said primary through tertiary amino and ammonio groups are primary through tertiary amino groups, more preferred are secondary and tertiary amino groups, particularly preferred are secondary amino groups. Thus, polyamines containing many secondary amino groups are preferred.

Examples of the polyalkylenepolyamine to be mentioned are polyethyleneimine, poly(ethyleneimine-co-N-methylethyleneamine), poly(N-methylethyleneamine), poly(ethyleneimine-co-N-ethylethyleneamine), polypropyleneimine, polybutyleneimine, poly(ethyleneimine-co-propyleneimine), poly(ethyleneimine-co-hexyleneimine), and the like.

Examples of the polyarylenepolyamine to be mentioned are polyphenyleneimine, poly(phenyleneimine-co-ethyleneimine), polyfurandiylimine, poly(furandiylimine-co-ethyleneimine), and the like.

As the polyamine (A), either one species or two or more different species can be used.

From the standpoint of epidermal regeneration accelerating effect and other reasons, the polyamine (A) is preferably a polyalkylenepolyamine, more preferably a polyethyleneimine.

The polyamine (A) can be produced by the following known methods and the like:

(1) the method which comprises subjecting an alkyleneimine (ethyleneimine, propyleneimine or the like) to ring-opening polymerization in the presence of a catalyst (carbon dioxide, hydrochloric acid, hydrobromic acid, p-toluenesulfonic acid, methanesulfonic acid, aluminum chloride, boron trifluoride or the like);

(2) the method which comprises subjecting an alkylene halide and/or arylene halide (ethylene chloride, propylene bromide or the like) and an alkylenediamine and/or arylenediamine (ethylenediamine, propylenediamine or the like) to polycondensation reaction;

(3) the method which comprises heating oxazolidone-2 or the like;

(4) the method which comprises extraction from a living body.

Among various types of the polyamine (A), the ammonio group-containing polyamine (A) can be obtained by subjecting the polyamine (A) prepared by any of the above methods (1) to (4) further to a treatment with an acid and/or a quaternizing agent.

Examples of the acid to be mentioned are mineral acids (hydrochloric acid, sulfuric acid, nitric acid, phosphoric acid, perchloric acid and the like), organic acids containing 1 to 4 carbon atoms (formic acid, acetic acid, butanoic acid, methanesulfonic acid and the like), and the like.

Examples of the quaternizing agent to be mentioned are alkyl halides containing 1 to 4 carbon atoms (methyl chloride, methyl bromide, methyl iodide, butyl bromide and the like), alkylsulfuric acids containing 2 to 6 carbon atoms (dimethylsulfuric acid, diethylsulfuric acid and the like), alkyl carbonates containing 2 to 6 carbon atoms (dimethyl carbonate, diethyl carbonate and the like), and the like.

The secondary amino and/or tertiary amino group-containing polyamine can also be obtained by treating a primary amino or secondary amino group-containing polyamine with the quaternizing agent.

The Mw of the polyamine (A) is 2,000 to 60,000, preferably 3,000 to 50,000, more preferably 4,000 to 40,000, particularly preferably 6,000 to 20,000. Within this range, the epidermal regeneration accelerating effect is further improved.

In the context of the invention, the weight average molecular weight (Mw) of the polyamine (A) is the value measured by gel permeation chromatography (GPC) using polyethylene glycol as the standard substance.

Examples of the form of said sheet (S) to be mentioned are film, foam (sponge), nonwoven cloth, woven cloth, knitted cloth, gels, and the like. Among these, film and foam are preferred and film is more preferred.

The thickness of the sheet (S) is preferably 1 μm to 5 cm, more preferably 5 μm to 1 cm, particularly preferably 15 μm to 3 mm, most preferably 30 to 500 μm.

The film or foam may have microfine pores all over or locally. These pores preferably have a size of the order easily permitting passage of air and water vapor. The size of the pores {the aperture area of the pore ($mm^2$)} is preferably 0.001 to 500 $mm^2$, more preferably 0.01 to 50 $mm^2$, particularly preferably 0.1 to 5 $mm^2$. As regards the shape of the aperture, it may be circular, elliptical, polygonal, e.g. triangular, rectangular or the like, or linear (slits), and the like.

The raw material of the sheet (S) is not restricted provided that cells and living bodies are not adversely affected thereby. As the sheet (S), a material which is ready to get dispersed or dissolved in a body fluid and the like or absorbed thereinto when applied to the wounded area and the like {hereinafter referred to as easily biodegradable material (S1)}, or a material which is hardly dispersed or dissolved in a body fluid and the like or absorbed thereinto when applied to the wounded area and the like {hereinafter referred to as hardly biodegradable material (S2)} can be employed. Moreover, the sheet (S) may be a combination of said easily biodegradable material (S1) and hardly biodegradable material (S2). Among these materials of the sheet (S), the hardly biodegradable material (S2) is preferred in consideration of the ease with which the wound dressing can be removed from the wound surface, and the like.

As the easily biodegradable material (S1), a natural polymer (S1A), a synthetic polymer (S1B), an inorganic material (S1C) and the like can be used.

Examples of the natural polymer (S1A) to be mentioned are collagen, gelatin, glycosaminoglycan, hyaluronic acid, chondroitin sulfate, keratan sulfate, dermathane sulfate, heparin, elastin, chitin, chitosan, fibrin, alginic acid, starch, dextran, albumin, polyhydroxybutyric acid, pectin, pectinic acid, galactan, pullulan, agarose, cellulose, gluten, fibroin, and the like.

Examples of the synthetic polymer (S1B) to be mentioned are (co)polymers of monomers selected from the group consisting of lactic acid, leucine, glycolic acid, ε-caprolactone, dioxanone, malic acid, lactide, and glycolide as essential monomer component (polyglycolic acids), synthetic polypeptides other than the polypeptide (P), and the like.

Examples of the inorganic material (S1C) to be mentioned are calcium carbonate (light calcium carbonate, heavy calcium carbonate, and the like), calcium phosphate {hydroxyapatite, tricalcium phosphate, mixtures thereof with other calcium phosphates (monocalcium hydrogenphosphate and the like), and the like}, and the like.

Among these, the natural polymer (S1A) and synthetic polymer (S1B) are preferred, the natural polymer (S1A) is more preferred, collagen, gelatin, hyaluronic acid, chitin, chitosan, fibrin, alginic acid, starch, dextran, agarose, cellulose, and fibroin are particularly preferred.

As the hardly biodegradable material (S2), a natural polymer (S2A), a synthetic polymer (S2B), an inorganic material (S2C) and the like can be used.

Examples of the natural polymer (S2A) to be mentioned are natural fibers (cotton, wool, linen, silk and the like) and the like.

Examples of the synthetic polymer (S2B) to be used are polyolefins (polyethylene, polypropylene, modification products thereof, and the like), olefin copolymers (ethylene-vinyl acetate copolymer, ethylene-ethyl (meth)acrylate copolymer, ethylene-methyl (meth)acrylate copolymer, ethylene-(meth)acrylic acid copolymer, and the like), polyurethane, polyester, polyacrylic acid, polyamide (nylons), polyvinyl chloride, polyvinylidene chloride, polystyrene, fluorocarbon resin, silicone resin, cellulose, viscose rayon, cuprammonium rayon, polyacetate, polyacrylonitrile, vinylon, vinylidene, and the like.

Examples of the inorganic material (S2C) to be used are metals (gold, silver, platinum, titanium, nickel and the like), ceramics (alumina, zirconia, aluminum nitride and the like), and the like.

Among these, the synthetic polymer (S2B) and the inorganic material (S2C) are preferred. More preferred is the synthetic polymer (S2B), particularly preferred are polyolefin, polyurethane, polyester, polyacrylic acid, polyamide (nylon), polystyrene, and silicone resin. The most preferred is polyurethane.

The polypeptide (P) and the sheet (S) can be bonded by a chemical bonding (an ionic bonding, a hydrogen bonding, a covalent bonding and/or the like) and/or physical adsorption (adsorption by van der Waals force, and the like).

Examples of the method of bonding the polypeptide (P) to the sheet (S) covalently to be mentioned are:

(1) the method which comprises reacting a polypeptide (P) having a primary amino or secondary amino group {a polypeptide (P) having arginine, histidine, isoleucine, leucine, methionine, phenylalanine, threonine, tryptophan, tyrosine, valine, alanine, asparagine, aspartic acid, glutamine, glutamic acid, proline, cysteine, lysine, serine, glycine, ornithine, histidine, 3-aminopropionic acid, 8-aminooctanoic acid and/or 20-aminoeicosanoic acid as constituent units, and the like polypeptide (P)} with a sheet (S) having a carboxyl group (a sheet made of a polyglycolic acid, a synthetic polypeptide not having the epidermal regeneration accelerating minimal amino acid sequence (X), a modified polyethylene or polypropylene, ethylene-(meth)acrylic acid copolymer, polyacrylic acid, collagen, gelatin, glycosaminoglycan, hyaluronic acid, chondroitin sulfate, dermathane sulfate, heparin, elastin, fibrin, alginic acid, albumin, pectin, pectinic acid, gluten and/or fibroin, and the like sheet);

(2) the method which comprises reacting the polypeptide (P) having a primary amino or secondary amino group with a sheet (S) having a hydroxyl group (a sheet made of polyglycolic acid, ethylene-vinyl acetate copolymer, polyurethane, polyester, cellulose, viscose rayon, cuprammonium rayon, polyacetate, polyacrylonitrile, vinylon, vinylidene, collagen, gelatin, glycosaminoglycan, hyaluronic acid, chondroitin sulfate, keratan sulfate, dermathane sulfate, heparin, elastin, chitin, chitosan, fibrin, alginic acid, starch, dextran, albumin, polyhydroxybutyric acid, pectin, pectinic acid, galactan, pullulan, agarose, gluten and/or fibroin, and the like sheet);

(3) the method which comprises reacting a polypeptide (P) having a hydroxyl group (a polypeptide (P) having aspartic acid, glutamic acid, serine, threonine, tyrosine, thyronine and/or hydroxypurine as constituent units, and the like polypeptide (P)) with the sheet (S) having a carboxyl group; and the like methods.

These reactions can be carried out in the known manner (the method described in Fundamentals and Experiments in Peptide Synthesis, published by Maruzen K.K., Oct. 5, 1997, and the like). Specific methods are described in the following paragraphs (1) to (3).

(1) In the case where the polypeptide (P) having a primary amino or secondary amino group is reacted with the sheet (S) having a carboxyl group, the carboxyl group in the sheet (S) is firstly reacted with a carbodiimide compound to give an acylisourea {R'—N=C(OCOR)—NH—R' (wherein —OCOR is the moiety derived from the sheet (S))}, and then the polypeptide (P) having a primary amino group or secondary amino group is added to the above acylisourea to cause the sheet (S) and the polypeptide (P) to be bonded together by an amide bonding.

Examples of the carbodiimide compound to be mentioned are N,N'-dicyclohexylcarbodiimide, 1-ethyl-3-(3-dimethylaminopropyl)carbodiimide hydrochloride and the like.

(2) In the case where the polypeptide (P) having a primary amino or secondary amino group is reacted with the sheet (S) having a hydroxyl group, the hydroxyl group in the sheet (S) is firstly reacted with a carbonyldiimidazole compound to give an imidazole derivative {R—Im, wherein Im represents an imidazoline ring and R is derived from the sheet (S)}, and then the polypeptide (P) having a primary amino or secondary amino group is added to said imidazole derivative to cause the sheet (S) and the polypeptide (P) to be bonded together by an N—C bonding.

Examples of the carbonyldiimidazole compound to be mentioned are N,N'-carbonyldiimidazole and the like.

(3) In the case where the polypeptide (P) having a hydroxyl group is reacted with the sheet (S) having a carboxyl group, the carboxyl group in the sheet (S) is firstly reacted with a carbodiimide compound to give an acylisourea, and then the polypeptide (P) having a hydroxyl group is added to said acylisourea to cause the sheet (S) and the polypeptide (P) to be bonded together by an ester bonding.

As the method of bonding the polypeptide (P) to the sheet (S) by physical adsorption, an ionic bonding, and/or a hydrogen bonding, there can be used a method which comprising putting the polypeptide (P) and the sheet (S) in a solvent or the like and admixing together. The solvent is not particularly restricted but there can be used an aqueous solution containing 0.001 to 50 weight % (preferably 0.01 to 10 weight %) of an inorganic salt, an organic acid salt, an acid and/or a base, and the like solvents.

Examples of the inorganic salt to be mentioned are metal halides, metal sulfates, metal phosphates, metal hydrogenphosphates, metal nitrates, metal carbonates, metal perhalogenates and the like. Specifically, for example, there can be mentioned sodium chloride, sodium sulfate, sodium phosphate, calcium chloride, iron nitrate, potassium chloride, magnesium sulfate, sodium carbonate, sodium hydrogenphosphate, potassium phosphate, potassium hydrogenphosphate, copper sulfate, iron sulfate, lithium chloride, sodium bromide, lithium bromide, sodium perchlorate, lithium perchlorate and the like.

Examples of the organic acid salt to be mentioned are sodium formate, sodium acetate, lithium acetate, sodium tartrate and the like.

Examples of the acid to be mentioned are inorganic acids, organic acids containing 1 to 6 carbon atoms, and the like. Specifically, for example, there can be mentioned hydrochloric acid, phosphoric acid, acetic acid, formic acid, phenol and sulfuric acid.

Examples of the base to be mentioned are inorganic bases, organic bases containing 2 to 6 carbon atoms, and the like. Specifically, for example, there can be mentioned sodium hydroxide, potassium hydroxide, ammonia and triethylamine.

Examples of the water to be mentioned are distilled water, deionized water, tap water, deionized distilled water and the like.

Among these solvents, an aqueous solution containing an inorganic salt, an acid and/or a base and water are preferred, and an aqueous solution containing an inorganic salt, an acid and/or a base is more preferred.

In terms of the strength of a bonding between the polypeptide (P) and the sheet (S), a chemical bonding is preferred and a covalent bonding is more preferred.

From the standpoint of epidermal regeneration accelerating effect and other reasons, the polypeptide (P) content of the wound dressing per unit surface area of the sheet (S) is preferably 0.1 $ng/cm^2$ to 100 $mg/cm^2$, more preferably 1 $ng/cm^2$ to 10 $mg/cm^2$, particularly preferably 10 $ng/cm^2$ to 1 $mg/cm^2$, most preferably 100 $ng/cm^2$ to 100 $\mu g/cm^2$.

In the context of the invention, the term "unit surface area" means the area of the sheet (S) surface to which cells are able to adhere. In this connection, a surface with minute irregularities preventing ingress of cells (e.g. not greater than 1 μm) is regarded as a smooth surface but when ribs or the like are provided for increasing the unit surface area, the surface areas of the ribs are included in the unit surface area.

The method of determining the polypeptide (P) content per unit surface area is not particularly restricted but, for example, immunological assay techniques can be employed. In the present invention, the polypeptide (P) content per unit surface area of the sheet (S) is represented by the value found by reacting a testpiece obtained by cutting off a part (e.g. a square area of 1 cm×1 cm) of the surface of the wound dressing with an enzyme-labeled anti-polypeptide (P) antibody and measuring the amount of the enzyme in the reacted enzyme-labeled antibody.

The enzyme-labeled antibody is usually one consisting of an enzyme and a specific antibody as bonded together by a chemical bonding (the two can be bonded by the known technology). Examples of the technology to be used are the method of bonding an enzyme (peroxidase, β-D-galactosidase, alkaline phosphatase, glucose-6-phosphate dehydrogenase, or the like) to the specific antibody by the glutaraldehyde method, periodic acid method, maleimide method, pyridyl disulfide method or the like (cf. Ishikawa, Eiji: Ultrahigh-sensitive enzyme immunoassay, Gakkaishuppan Center K.K., 1993; Enzyme Immunoassay, translated by Ishikawa, Eiji, Tokyo Kagaku Dojin K.K., 1989; and Enzyme-labeled antibody method, edited by Watanabe, Keiichi et al.; Gakusai Kikaku K.K., 1992).

The specific antibody mentioned above is an antibody which binds specifically to the polypeptide (P) {the known methods, namely the polyclonal antibody preparation method and monoclonal antibody preparation method (Enzyme Immunoassay, translated by Ishikawa, Eigi, Tokyo Kagaku Dojin K.K., 1989; the Enzyme-labeled antibody method, edited by Watanabe, Keiichi et al., Gakusai Kikaku K.K., 1992); and the like can be used}. The affinity constant of the specific antibody for cross-reacting antigens is preferably as small as possible. By way of illustration, assuming that the affinity constant of the specific antibody for the polypeptide (P) is 1, the affinity constant for cross-reacting antigens is preferably not more than 1, more preferably not more than 0.1, particularly preferably not more than 0.01. The affinity constant referred to above can be determined by the method described in Enzyme Immunoassay (translated by Ishikawa, Eigi, Tokyo Kagaku Dojin K.K., 1989).

The polyamine (A) is preferably bonded to the sheet (S) and/or the polypeptide (P).

Examples of the method to be used for bonding the polyamine (A) to the sheet (S) and/or the polypeptide (P) are the chemical reaction methods, physical adsorption methods {the same methods as the above-described methods for bonding the polypeptide (P) and the sheet (S)} and the like methods.

The polyamine (A) content (number/cm$^2$) of the wound dressing in terms of the average number of amino groups per unit area of the sheet (S) is preferably $10^8$ to $10^{22}$, more preferably $10^{10}$ to $10^{20}$, from the standpoint of epidermal regeneration accelerating effect.

The average number of amino groups can be determined by the known methods, for example the trinitrobenzenesulfonic acid (TNBS) method {Protein Chemistry IV (Tokyo Kagaku Dojin, 1981) and the like} and the total amine determination by hydrochloric acid-indicator (bromphenol blue or the like) titrimetry (JIS K7237-1986, ASTM D2074-66 and the like), and the like.

Specifically, in the present invention, the average number of amino groups (number/cm$^2$) per unit area of the sheet (S) can be determined as follows. By using the TNBS method, a calibration curve (the number of amino groups plotted against absorbance) is constructed for a polyamine (A) having a known number of amino groups or a solution thereof.

The testpiece prepared by cutting off a part (e.g. a square area of 1 cm×1 cm) of the surface of the wound dressing is measured for absorbance by the TNBS method and the absorbance is converted to the number of amino groups using said calibration curve.

Where necessary, the wound dressing of the invention may be sterilized. Examples of the sterilization method to be used are radiation, ethylene oxide gas, plasma, γ-ray, alcohol, autoclaving, dry heat sterilization and the like methods. Any of these methods may be used alone or two or more of these methods may be used in combination.

Insofar as the wound surface may be successfully covered, the wound dressing of the invention can be applied without any restriction. This wound dressing may be fixedly secured in position with the aid of a cover carrying an adhesive or self-adhesive agent, a bandage, an expandable mesh tape, an eye patch, or the like, or sutured or bonded. Furthermore, this wound dressing may be used in combination with one or more of other therapeutic agents for wounds (an ointment, cream, powder, antibacterial agent, iodine preparation, wound dressing, artificial dermis, cell growth factor and the like).

The term "wound" is used herein to mean any damaged skin inclusive of a burn, decubitus, ulcer, trauma, and injury caused by a dermatome.

The wound dressing of the invention is not only applicable to wounds requiring epidermal regeneration but also applicable to partial or full-thickness epidermal defects.

The method for epidermal regeneration treatment according to the invention is characterized by using said wound dressing.

The wound dressing of the invention has an extremely high epidermal regeneration accelerating effect. Therefore, the film of the invention is suited for the therapy of defected skin wounds (decubitus, ulcer, burn, trauma, injury cased by a dermatome). Therefore, the wound dressing of the invention is free from such troubles as formation of cicatrices, requirement for epidermal transplanting and the like to be capable of treating wounds without burdens on patients.

BEST MODE FOR CARRYING OUT THE INVENTION

The following examples are intended to further illustrate the present invention without defining the scope of the invention. Unless otherwise indicated, % invariably means weight %.

Example 1

(1) Preparation of an Aqueous Solution of ProNectin F

A solution composed of 2.5 mg of ProNectin F (product of Sanyo Chemical Industries, Ltd.), which contains the Arg Gly Asp sequence (1) and the (Gly Ala Gly Ala Gly Ser)$_9$ sequence (8) each in the number of about 13 and has a Mw of about 110,000, and 2.5 mL of 4.5 M aqueous lithium perchlorate solution was diluted 20-fold with 0.02 M phosphate buffer solution (pH 7.2) (briefly, PBS) containing 99.5% sodium chloride at a concentration of 0.85% to prepare an aqueous P1 solution (ProNectin F concentration 50 μg/mL).

(2) Preparation of an Aqueous Solution of Polyethyleneimine 10,000

In 1 mL of deionized water was dissolved 10 mg of polyethyleneimine (Mw 10,000, product of Wako Pure Chemical Industries) to prepare an aqueous solution of polyethyleneimine 10,000 (polyethyleneimine concentration: 10 mg/mL).

(3) Preparation of a Sheet (B1)

An aqueous urethane solution prepared from 6.67 g of water-soluble urethane (Permarin UA200, product of Sanyo Chemical Industries, Ltd.) and 3.33 g of deionized water was coated on a polypropylene sheet (product of Medical Agent K.K.), 20 cm (length)×20 cm (width)×1 mm (thick), to prepare a coated sheet. This coated sheet was allowed to sit at room temperature (about 25° C.) for 24 hours, and then dried in a fair-wind dryer at 120° C. for 1 hour to prepare a dry sheet. Then, an urethane film {a sheet (B1)} was isolated by peeling it off the dry sheet.

(4) Preparation of an Epidermal Regeneration Accelerating Wound Dressing (PB1)

In 50 mL of deionized water was dissolved 0.479 g of 1-ethyl-3-(3-dimethylaminopropyl)carbodiimide hydrochloride (product of Sigma) to give an aqueous carbodiimide solution. This aqueous carbodiimide solution, 50 mL, and a 10 cm×10 cm patch of the sheet (B1) were placed in a glass dish and allowed to sit at 25° C. for 1 hour to prepare a treated sheet. Thereafter, this treated sheet was washed 5 times with 100 mL portions of deionized water, put in 50 mL of the aqueous P1 solution in a glass dish, and allowed to sit at 25° C. for 30 minutes. After that, 0.5 mL of the aqueous solution of polyethyleneimine 10,000 was poured in the glass dish and allowed to stand at 25° C. for a further 30 minutes to prepare a composite sheet. Then, this composite sheet was washed 5 times with 100 mL portions of deionized water and dried in a fair-wind dryer at 37° C. for 12 hours to give an epidermal regeneration accelerating wound dressing (PB1) (deposition amount of ProNectin F: ca 1 $\mu g/cm^2$).

Example 2

(1) Preparation of an Aqueous Solution of ProNectin F2

A solution composed of 2.5 mg of ProNectin F2 (product of Sanyo Chemical Industries, Ltd.), which contains the Arg Gly Asp sequence (1) and the (Gly Ala Gly Ala Gly Ser)$_3$ sequence (7) each in the number of about 5 and has a Mw of about 20,000, and 2.5 mL of 4.5 M aqueous lithium perchlorate solution was diluted 20-fold with 0.02 M phosphate buffer solution (pH 7.2) (briefly, PBS) containing 99.5% sodium chloride at a concentration of 0.85% to prepare an aqueous P2 solution (ProNectin F2 concentration: 50 $\mu g/mL$).

(2) Preparation of an Epidermal Regeneration Accelerating Wound Dressing (PB2)

Using the above aqueous P2 solution in lieu of said aqueous P1 solution, the procedure of Example 1 was otherwise repeated to prepare an epidermal regeneration accelerating wound dressing (PB2)(deposition amount of ProNectin F2: ca 1 $\mu g/cm^2$).

Example 3

(1) Preparation of an Aqueous Solution of ProNectin F3

A solution composed of 2.5 mg of ProNectin F3 (product of Sanyo Chemical Industries, Ltd.), which contains the Arg Gly Asp sequence (1) and the (Gly Val Pro Gly Val)$_2$ Gly Gly (Gly Ala Gly Ala Gly Ser)$_3$ sequence (49) each in the number of about 3 and has a Mw of about 10,000, and 2.5 mL of 4.5 M aqueous lithium perchlorate solution was diluted 20-fold with 0.02 M phosphate buffer solution (pH 7.2) (briefly, PBS) containing 99.5% sodium chloride at a concentration of 0.85% to prepare an aqueous P3 solution (ProNectin F3 concentration: 50 $\mu g/mL$).

(2) Preparation of an Epidermal Regeneration Accelerating Wound Dressing (PB3)

Using the above aqueous P3 solution in lieu of said aqueous P1 solution, the procedure of Example 1 was otherwise repeated to prepare an epidermal regeneration accelerating wound dressing (PB3)(deposition amount of ProNectin F3: ca 1 $\mu g/cm^2$)

Example 4

(1) Preparation of an Aqueous Solution of ProNectin L

A solution composed of 2.5 mg of ProNectin L (product of Sanyo Chemical Industries, Ltd.), which contains the Ile Lys Val Ala Val sequence (2) and the (Gly Ala Gly Ala Gly Ser)$_9$ sequence (8) each in the number of about 13 and has a Mw of about 110,000, and 2.5 mL of 4.5 M aqueous lithium perchlorate solution was diluted 20-fold with 0.02 M phosphate buffer solution (pH 7.2) (briefly, PBS) containing 99.5% sodium chloride at a concentration of 0.85% to prepare an aqueous P4 solution (ProNectin L concentration: 50 $\mu g/mL$).

(2) Preparation of an Epidermal Regeneration Accelerating Wound Dressing (PB4)

Using the above aqueous P4 solution in lieu of said aqueous P1 solution, the procedure of Example 1 was otherwise repeated to prepare an epidermal regeneration accelerating wound dressing (PB4)(deposition amount of ProNectin L: ca 1 $\mu g/cm^2$).

Example 5

(1) Preparation of an Aqueous Solution of Polyethyleneimine 55,000

A solution of 10 mg of polyethyleneimine 50,000 to 100,000 (weight average molecular weight 50,000 to 100,000, product of ICN Biomedicals Inc.) in 1 mL of deionized water was subjected to Superdex (product of Amersham Pharmacia) gel filtration and a fraction corresponding to the weight average molecular weight of 50,000 to 60,000 was recovered. The recovered solution was concentrated by ultrafiltration to give an aqueous solution of polyethyleneimine 55,000 (Mw 55,000, polyethyleneimine concentration: 10 mg/mL).

(2) Preparation of an Epidermal Regeneration Accelerating Wound Dressing (PB5)

Using the above aqueous solution of polyethyleneimine 55,000 in lieu of said aqueous solution of polyethyleneimine 10,000, the procedure of Example 1 was otherwise repeated to prepare an epidermal regeneration accelerating wound dressing (PB5) (deposition amount of ProNectin F: ca 1 $\mu g/cm^2$).

Example 6

(1) Preparation of an Aqueous Solution of Polyethyleneimine 5,000

In 1 mL of deionized water was dissolved 20 mg of 50% aqueous polyethyleneimine solution (weight average molecular weight 50 to 60,000, product of Acros Organ ICN). The resulting solution was subjected to Superdex (product of Amersham Pharmacia) gel filtration and a fraction corresponding to the weight average molecular weight of 3,000 to 7,000 was recovered. The recovered solution was concentrated by ultrafiltration to give an aqueous solution of polyethyleneimine 5,000 (Mw 5,000, polyethyleneimine concentration: 10 mg/mL).

(2) Preparation of an Epidermal Regeneration Accelerating Wound Dressing (PB6)

Using the above aqueous solution of polyethyleneimine 5,000 in lieu of said aqueous solution of polyethyleneimine 10,000, the procedure of Example 1 was otherwise repeated to prepare an epidermal regeneration accelerating wound dressing (PB6) (deposition amount of ProNectin F: ca 1 μg/cm$^2$).

Example 7

(1) Preparation of an Aqueous Solution of Tertiarized Polyethyleneimine 10,000

To 100 mL of aqueous solution of polyethyleneimine 10,000 (10 mg/mL) were added 0.5 g of methyl chloride and 1.5 g of potassium hydroxide, and the reaction was carried out at 80° C. for 8 hours. After completion of this reaction, the reaction mixture was dialyzed against water through a dialysis membrane, and the dialyzate was concentrated by ultrafiltration to give an aqueous solution of tertiarized polyethyleneimine 10,000 (Mw 10,000, tertiarized polyethyleneimine concentration: 10 mg/mL).

(2) Preparation of an Epidermal Regeneration Accelerating Wound Dressing (PB7)

Using the above aqueous solution of tertiarized polyethyleneimine 10,000 in lieu of said aqueous solution of polyethyleneimine 10,000, the procedure of Example 1 was otherwise repeated to prepare an epidermal regeneration accelerating wound dressing (PB7) (deposition amount of ProNectin F: ca 1 μg/cm$^2$).

Comparative Example 1

(1) Preparation of an Aqueous Solution of Polyethyleneimine 1,800

In 1 mL of deionized water was dissolved 10 mg of polyethyleneimine (Mw 1,800, product of Wako Pure Chemical Industries, Ltd.) to give an aqueous solution of polyethyleneimine 1,800 (polyethyleneimine concentration: 10 mg/mL).

(2) Preparation of a Wound Dressing (HB1)

Using the above aqueous solution of polyethyleneimine 1,800 in lieu of said aqueous solution of polyethyleneimine 10,000, the procedure of Example 1 was otherwise repeated to prepare a wound dressing (HB1) (deposition amount of ProNectin F: ca 1 μg/cm$^2$)

Comparative Example 2

(1) Preparation of an Aqueous Solution of Polyethyleneimine 75,000

A solution of 10 mg of polyethyleneimine 50,000 to 100,000 (weight average molecular weight 50,000 to 100,000, product of ICN Biomedicals Inc.) in 1 mL of deionized water was subjected to Superdex (product of Amersham Pharmacia) gel filtration and a fraction corresponding to the weight average molecular weight of 70,000 to 80,000 was recovered. The recovered solution was concentrated by ultrafiltration to give an aqueous solution of polyethyleneimine 75,000 (Mw 75,000, polyethyleneimine concentration: 10 mg/mL).

(2) Preparation of a Wound Dressing (HB2)

Using the above aqueous solution of polyethyleneimine 75,000 in lieu of said aqueous solution of polyethyleneimine 10,000, the procedure of Example 1 was otherwise repeated to prepare a wound dressing (HB2) (deposition amount of ProNectin F: ca 1 μg/cm$^2$).

Comparative Example 3

(1) Preparation of an Aqueous poly-L-lysine Solution

In 1 mL of deionized water was dissolved 10 mg of poly-L-lysine (Mw 50,000, product of Wako Pure Chemical Industries, Ltd.) to give an aqueous poly-L-lysine solution (poly-L-lysine concentration: 10 mg/mL).

(2) Preparation of a Wound Dressing (HB3)

Using the above aqueous poly-L-lysine solution in lieu of said aqueous solution of polyethyleneimine 10,000, the procedure of Example 1 was otherwise repeated to prepare a wound dressing (HB3) (deposition amount of ProNectin F: ca 1 μg/cm$^2$).

Comparative Example 4

(1) Preparation of an Aqueous Solution of poly(dimethylaminoethyl methacrylate) 15,000

In a 10 ml test tube were placed 2 g of dimethylaminoethyl methacrylate, 0.04 g of azobisisovaleronitrile, and 2 g of dioxane, and after nitrogen purging and hermetic sealing, the tube was shaken in a hot water bath at 70° C. for 4 hours. The resulting solution was dropped into 100 mL of hexane to let the polymer separate out. This polymer was dried to give a poly(dimethylaminoethyl methacrylate) (DAE polymer). The DAE polymer was dissolved in deionized water and the solution was subjected to Superdex (product of Amersham Pharmacia) gel filtration to recover a fraction corresponding to the molecular weight of 10,000 to 20,000. The recovered solution was concentrated by ultrafiltration to give an aqueous solution of DAE polymer 15,000 (Mw 15,000, DAE polymer concentration: 10 mg/mL).

(2) Preparation of an Epidermal Regeneration Accelerating Wound Dressing (PB6)

Using the above aqueous solution of DAE polymer 15,000 in lieu of said aqueous solution of polyethyleneimine 10,000, the procedure of Example 1 was otherwise repeated to prepare an epidermal regeneration accelerating wound dressing (PB6) (deposition amount of ProNectin F: ca 1 μg/cm$^2$).

Comparative Example 5

(1) Preparation of an Aqueous Solution of Quaternized DAE polymer 15,000

In a 10 ml test tube were placed 2 g of dimethylaminoethyl methacrylate, 0.04 g of azobisisovaleronitrile, and 2 g of dioxane, and after nitrogen purging and hermetic sealing, the tube was shaken in a hot water bath at 70° C. for 4 hours. The resulting solution was dropped into 100 mL of hexane to let the polymer separate out. The polymer was dried to give a poly(dimethylaminoethyl methacrylate) (DAE polymer) and this DAE polymer was dissolved in deionized water (10 mg/mL). To 100 mL of the solution thus obtained, 5 g of methyl chloride was added and reacted at 80° C. for 8 hours to prepare an aqueous solution of quaternized DAE polymer. This aqueous solution of quaternized DAE polymer was subjected to Superdex (product of Amersham Pharmacia) gel filtration to recover a fraction corresponding to the molecular weight of 10,000 to 20,000. The recovered solution was conquaternized DAE polymer 15,000 (Mw 15,000, quaternized DAE polymer concentration: 10 mg/mL).

(2) Preparation of an Epidermal Regeneration Accelerating Wound Dressing (PB7)

Using the above aqueous solution of quaternized DAE polymer 15,000 in lieu of said aqueous solution of polyethyleneimine 10,000, the procedure of Example 1 was otherwise repeated to prepare an epidermal regeneration accelerating wound dressing (PB7) (deposition amount of ProNectin F: ca 1 μg/cm$^2$)

Comparative Example 6

(1) Preparation of a Wound Dressing (HB6)

Except that said aqueous solution of polyethyleneimine 10,000 was not used, the procedure of Example 1 was repeated to prepare a wound dressing (HB6)(deposition amount of ProNectin F: ca 1 μg/cm$^2$)

Comparative Example 7

The sheet (B1) was used as a wound dressing for comparison.

Comparative Example 8

Bioclusive (product of Johnson & Johnson, a polyurethane film) was used as a wound dressing for comparison (B2).

<Evaluation 1 (Cultured Skin)>

From each of the wound dressings according to Examples 1 to 7 and Comparative Examples 1 to 8, a disk measuring 2 cm in diameter was cut out and sterilized by 2-hour-long UV irradiation in a clean bench.

On the other hand, a cultured dermis was prepared using the three-dimensional cultured tissue construction kit "Pre Tissue-Skin 1" (product of Toyobo Co., Ltd.) in accordance with the kit manual thereof. In the central region of this cultured dermis, epidermal cells were seeded to prepare a cultured skin.

Then, Epidermal Medium was added to the height of the cultured skin. On the top of this cultured skin was placed the wound dressing disk obtained above. The cultured skin was then cultured in an incubator (5 volume % $CO_2$ concentration) at 37° C. for 4 days.

After 4 days of cultivation, the Epidermal Medium was discarded and A/L medium (Air/Liquid Culture Medium) was added up to the height of the cultured skin. The cultured skin was further cultured for 7 days.

Thereafter, the wound dressing was peeled off the upper surface of the cultured skin and the cultured skin was fixed in formalin and embedded in paraffin to give a tissue section. This tissue section was treated with hematoxylin-eosin stain (H-E stain) and the status of epidermal regeneration of the cultured skin was evaluated.

<Evaluation Criteria>

Excellent: Epidermal cells are stratified all over the upper surface of the dermis showing an overall epidermal regeneration.

Fair: Epidermal cells are stratified on part of the upper surface of the dermis showing a partial regeneration of the epidermis.

Poor: Epidermal cells are present on the upper surface of the dermis but not stratified showing no epidermal regeneration.

TABLE 1

|  |  | Wound dressing | Epidermal regeneration |
|---|---|---|---|
| Example | 1 | PB1 | Excellent |
|  | 2 | PB2 | Excellent |
|  | 3 | PB3 | Excellent |
|  | 4 | PB4 | Excellent |
|  | 5 | PB5 | Excellent |
|  | 6 | PB6 | Excellent |
|  | 7 | PB7 | Excellent |
| Comparative Example | 1 | HB1 | Fair |
|  | 2 | HB2 | Fair |
|  | 3 | HB3 | Poor |
|  | 4 | HB4 | Poor |
|  | 5 | HB5 | Poor |
|  | 6 | HB6 | Poor |
|  | 7 | B1 | Poor |
|  | 8 | B2 | Poor |

It is clear from the results presented in Table 1 that whereas an overall epidermal regeneration could be seen in Examples 1 to 7 using the epidermal regeneration accelerating wound dressings (PB1) to (PB7) according to the invention, only a partial epidermal regeneration or no regeneration at all was seen in Comparative Examples 1 to 8 using the wound dressings for comparison, (HB1) to (HB6), (B1) and (B2).

<Evaluation 2 (Animal Experiment)>

After DM mice (C57BLK Jc1 db/db, produced by Clea Japan, Inc.) were inhalation-anesthetized with diethyl ether, the hairs of the entire back were shaved off with Feather razor and a round (1.4 cm in diameter) full-thickness skin defect wound was made in the central region. Incidentally, the onset of diabetes in these DM mice was confirmed by using the diabetes test strip (Uropiece, product of Fujisawa Pharmaceutical Co., Ltd.).

(1) Application of the Wound Dressing (PB1) of Example 1

A 2 cm×2 cm cutting of the wound dressing (PB1) of Example 1 was stuck to Bioclusive (product of Johnson & Johnson) and, with the wound dressing being abutted against the wound surface, the laminate was applied to the full-thickness skin defect wound of each DM mouse. In addition, for increasing the adhesion to the wound surface, a wad of absorbent cotton was superimposed and wrapped around the trunk of the animal with a self-adhesive bandage (Silkytex, product of Alcare K.K.). The DM mice were housed in a room controlled at 24° C., with free access to food and drinking water. On day 3 after the start of the experiment, the wound dressing was removed from the wound surface and the wound dressing (PB1) was applied again together with the Bioclusive.

(2) Application of the Wound Dressing (B1) of Comparative Example 7 and a Trafermin Solution:

In 2.5 mL of saline was dissolved 250 μg of Fiblast Spray 250 (product of Kaken Pharmaceutical Co., Ltd.), which is a therapeutic agent for decubitus/skin ulcer, to prepare a trafermin solution of 100 μg/mL concentration.

Except that the wound dressing (B1) of Comparative Example 7 was used in lieu of the wound dressing (PB1) and that, prior to laminating the wound dressing (B1) to the wound dressing, 0.2 mL of trafermin solution (corresponding to 20 μg of trafermin) was dropped from a pipette onto the full-thickness skin defect wound, DM mouse nurture was started in the same manner as above (1). On day 3 after the start of the experiment, the wound dressing was removed from the wound surface and 0.2 mL of the trafermin solution was dropped onto the defect wound. Thereafter, the wound dressing (B1) was applied again together with the Bioclusive.

(3) Application of the Wound Dressing (B2) of Comparative Example 8

The wound dressing (B2) of Comparative Example 8 was applied intimately to the wound surface. For increasing the adhesion to the wound surface, a wad of absorbent cotton was superimposed and wrapped around the animal's trunk with a self-adhesive bandage (Silkytex, product of Alcare K.K.). DM mouse nurture was started in the same manner as above (1). On day 3 after the start of the experiment, the wound dressing was removed from the wound surface and the wound dressing (B2) was applied again.

(4) Observation of the Status of Wound Healing

Figure 2:
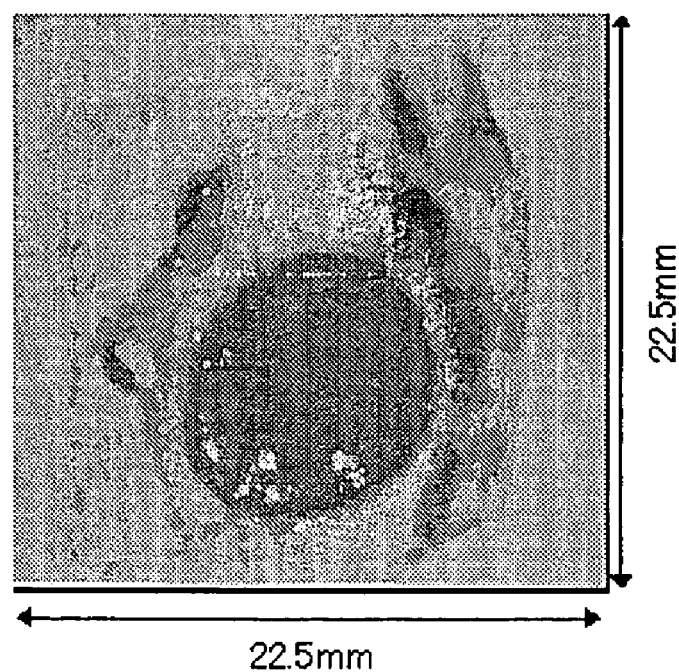
FIG. 2 is a photograph showing the status of wound healing in DM mice on day 7 by using the wound dressing of Comparative Example 7.
Figure 3:
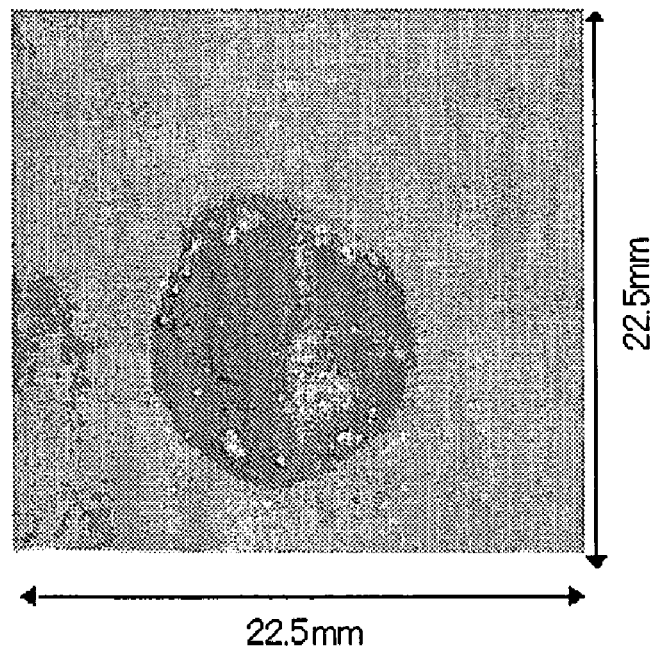
FIG. 3 is a photograph showing the status of wound healing in DM mice on day 7 by using the wound dressing of Comparative Example 8.
Figure 4:
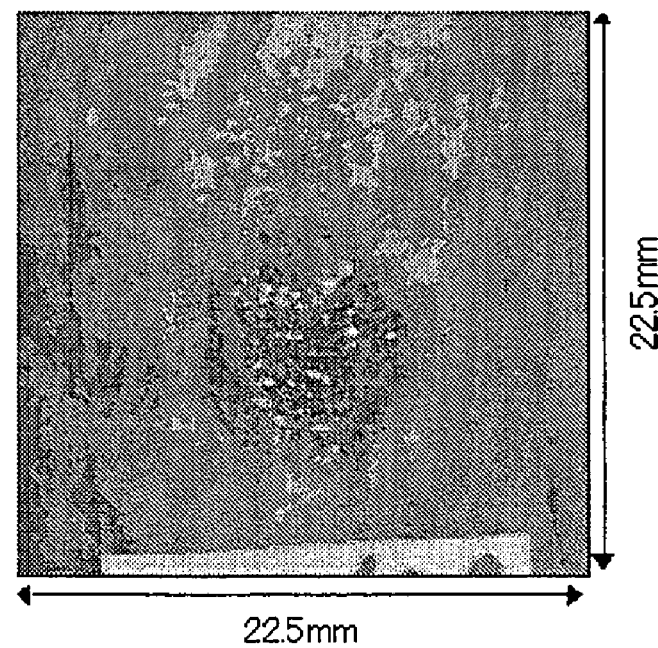
FIG. 4 is a photograph showing the status of wound healing in DM mice on day 14 by using the wound dressing of Example 1.
Figure 5:
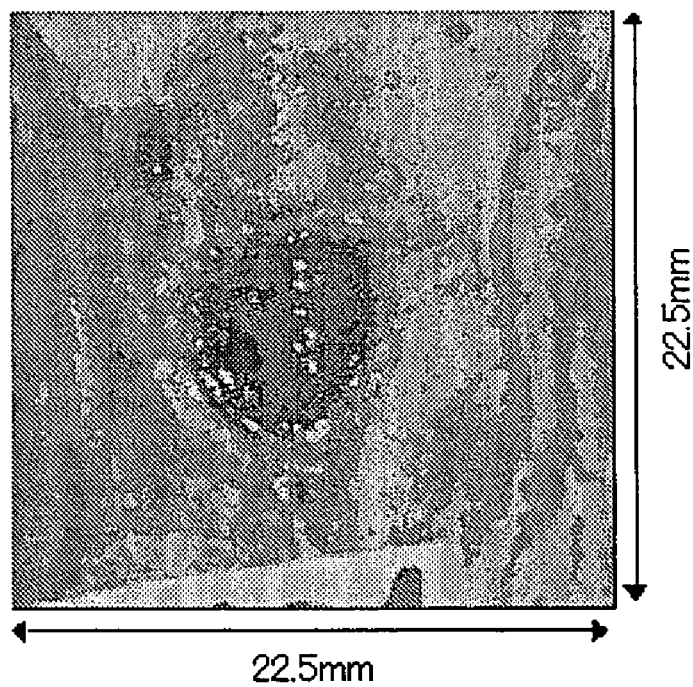
FIG. 5 is a photograph showing the status of wound healing in DM mice on day 14 by using the wound dressing of Comparative Example 7.
Figure 6:
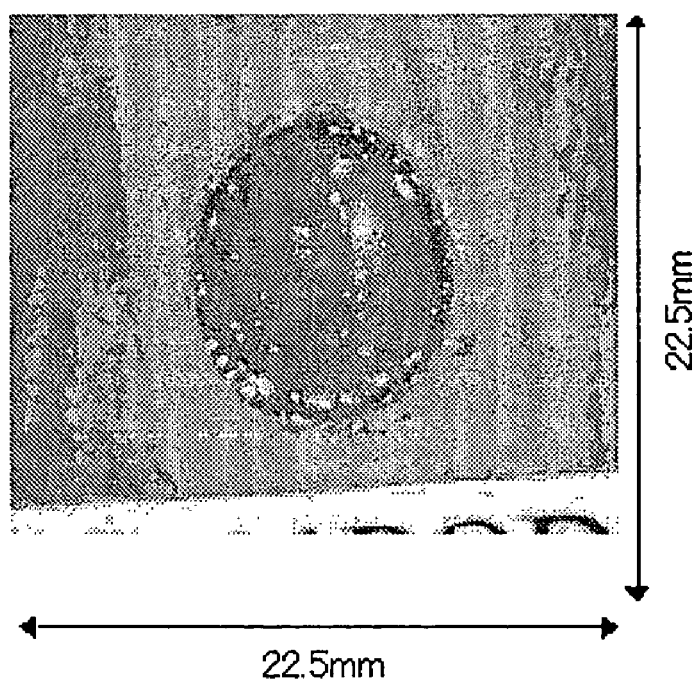
FIG. 6 is a photograph showing the status of wound healing in DM mice on day 14 by using the wound dressing of Comparative Example 8.

On day 7 and day 14 after the start of animal nurture, the wound dressing was removed from the wound surface and the wound surface was macroscopically examined. The photographs are presented in FIG. 1 [day 7, wound dressing (PB1)], FIG. 2 [day 7, wound dressing (B1)+trafermin solution], FIG. 3 [day 7, wound dressing (B2)], FIG. 4 [day 14, wound dressing (PB1)], FIG. 5 [day 14, wound dressing (B1)+trafermin solution] and FIG. 6 [day 14, wound dressing (B2)].

Referring to the results on day 7, the use of the wound dressing (PB1) according to Example 1 of the invention (FIG. 1) led to the finding of epidermal regeneration from the entire margin of the wound. On the other hand, neither the use of the wound dressing (B1) of Comparative Example 7 plus trafermin solution (FIG. 2) nor the use of the wound dressing (B2) of Comparative Example 8 (FIG. 3) resulted in epidermal regeneration.

Referring to the results on day 14, the use of the wound dressing (PB1) according to Example 1 of the invention (FIG. 4) resulted in epidermal regeneration all over the wound surface. On the other hand, the use of the wound dressing (B1) of Comparative Example 7 plus trafermin solution (FIG. 5) resulted in epidermal regeneration on part of the wound surface but not all over it. The use of the wound dressing (B2) of Comparative Example 8 (FIG. 6) led to no epidermal regeneration. Thus, whereas the wound could be completely healed with the wound dressings of the invention, quite an inadequate wound healing could be obtained with any of the wound dressings for comparison.

---

The invention claimed is:

1. A wound dressing for accelerating epidermal regeneration which comprises:
   at least one polypeptide (P),
   a polyalkylenepolyamine and/or polyarylenepolyamine (A) having a weight average molecular weight of 2,000 to 60,000, and
   a sheet (S) being polyurethane,
   wherein the at least one polypeptide (P) is selected from the group consisting of a polypeptide represented by SEQ ID NO: 50 and a polypeptide represented by SEQ ID NO: 51,
   wherein the at least one polypeptide (P) and the sheet (S) are bonded by a covalent bonding.

2. The wound dressing according to claim 1 wherein the polyalkylenepolyamine and/or polyarylenepolyamine (A) is a polyethyleneimine.

3. A method for epidermal regeneration treatment which comprises applying the wound dressing according to claim 1.

4. The wound dressing according to claim 1, wherein the at least one polypeptide (P) is the polypeptide represented by SEQ ID NO: 50.

5. The wound dressing according to claim 1, wherein the at least one polypeptide (P) is the polypeptide represented by SEQ ID NO: 51.

* * * * *